(12) United States Patent
Gabriel et al.

(10) Patent No.: US 11,413,398 B2
(45) Date of Patent: Aug. 16, 2022

(54) ELECTRONIC INJECTOR FOR INJECTING A MEDICINAL PRODUCT

(71) Applicant: HASELMEIER AG, St. Gallen (CH)

(72) Inventors: Frederic Gabriel, Zurich (CH); Sascha Pohl, Wildberg (DE)

(73) Assignee: MEDMIX SWITZERLAND AG, Haag (CH)

( * ) Notice: Subject to any disclaimer, the term of this patent is extended or adjusted under 35 U.S.C. 154(b) by 372 days.

(21) Appl. No.: 16/100,014

(22) Filed: Aug. 9, 2018

(65) Prior Publication Data

US 2019/0091412 A1 Mar. 28, 2019

Related U.S. Application Data

(60) Provisional application No. 62/564,531, filed on Sep. 28, 2017.

(51) Int. Cl.
*A61M 5/14* (2006.01)
*A61M 5/315* (2006.01)
(Continued)

(52) U.S. Cl.
CPC .... *A61M 5/31585* (2013.01); *A61M 5/14244* (2013.01); *A61M 5/20* (2013.01);
(Continued)

(58) Field of Classification Search
CPC .......... A61M 5/31585; A61M 5/14244; A61M 5/20; A61M 5/31546; A61M 5/3157;
(Continued)

(56) References Cited

U.S. PATENT DOCUMENTS 5,383,865 A * 1/1995 Michel ................ A61M 5/3158
604/232
5,827,232 A 10/1998 Chanoch et al.
(Continued)

FOREIGN PATENT DOCUMENTS

WO 02092153 A2 11/2002
WO WO-2017189707 A1 * 11/2017 ........... A61B 5/6833

OTHER PUBLICATIONS

International search report and written opinion dated Feb. 4, 2019 of corresponding international application PCT/EP2018/074741.

*Primary Examiner* — Nathan R Price
*Assistant Examiner* — Tania Ismail
(74) *Attorney, Agent, or Firm* — Global IP Counselors, LLP

(57) ABSTRACT

An example injector includes a rotary knob for selecting a function and setting a dosing quantity for an injection, a button located on an end of the rotary knob for initiating the injection, an electric motor, an encoder for evaluating output rotary motion of the motor, and a processor that converts the dosing quantity into a number of encoder pulses and controls operation of the motor based on the number of encoder pulses when dosage is triggered. The injector also includes a transmission coupled to the electric motor to convert a speed of the motor, a threaded spindle coupled to the transmission that moves linearly based on the output rotary motion of the motor at the speed as converted by the transmission, and a punch connected to an end of the threaded spindle. The linear movement of the spindle causes the punch to release medicament.

31 Claims, 19 Drawing Sheets

(51) Int. Cl.
*A61M 5/20* (2006.01)
*A61M 5/48* (2006.01)
*A61M 5/142* (2006.01)
*A61M 5/24* (2006.01)

(52) U.S. Cl.
CPC ............ *A61M 5/24* (2013.01); *A61M 5/3157* (2013.01); *A61M 5/31546* (2013.01); *A61M 5/31556* (2013.01); *A61M 5/31568* (2013.01); *A61M 5/31575* (2013.01); *A61M 5/31576* (2013.01); *A61M 5/482* (2013.01); *A61M 5/3158* (2013.01); *A61M 5/3159* (2013.01); *A61M 5/31525* (2013.01); *A61M 5/31545* (2013.01); *A61M 5/31593* (2013.01); *A61M 2005/31518* (2013.01); *A61M 2005/31588* (2013.01); *A61M 2205/215* (2013.01); *A61M 2205/332* (2013.01); *A61M 2205/3365* (2013.01); *A61M 2205/3561* (2013.01); *A61M 2205/502* (2013.01); *A61M 2205/505* (2013.01); *A61M 2205/581* (2013.01); *A61M 2205/582* (2013.01); *A61M 2205/583* (2013.01); *A61M 2205/80* (2013.01); *A61M 2205/8206* (2013.01)

(58) Field of Classification Search
CPC ............ A61M 5/482; A61M 5/31545; A61M 5/31593; A61M 5/3158; A61M 5/3159; A61M 2005/31588; A61M 2205/3365; A61M 2205/505
See application file for complete search history.

(56) References Cited

U.S. PATENT DOCUMENTS

| | | | |
|---|---|---|---|
| 6,585,698 | B1 | 7/2003 | Packman et al. |
| 8,381,719 | B1* | 2/2013 | Lawrence ......... A61M 15/0075 128/200.23 |
| 2002/0055720 | A1* | 5/2002 | Hohlfelder ............. A61M 5/20 604/232 |
| 2007/0144514 | A1* | 6/2007 | Yeates ................... B01D 45/08 128/203.15 |
| 2007/0197854 | A1* | 8/2007 | Marseille ............... A61M 60/50 600/16 |
| 2014/0163474 | A1* | 6/2014 | Draper .................. G05B 11/00 604/189 |
| 2016/0303326 | A1* | 10/2016 | Binier .................... A61M 5/31 |
| 2016/0346478 | A1 | 12/2016 | Bar-El et al. |
| 2017/0043098 | A1 | 2/2017 | Kohlbrenner et al. |
| 2017/0128673 | A1 | 5/2017 | Marsh et al. |

* cited by examiner

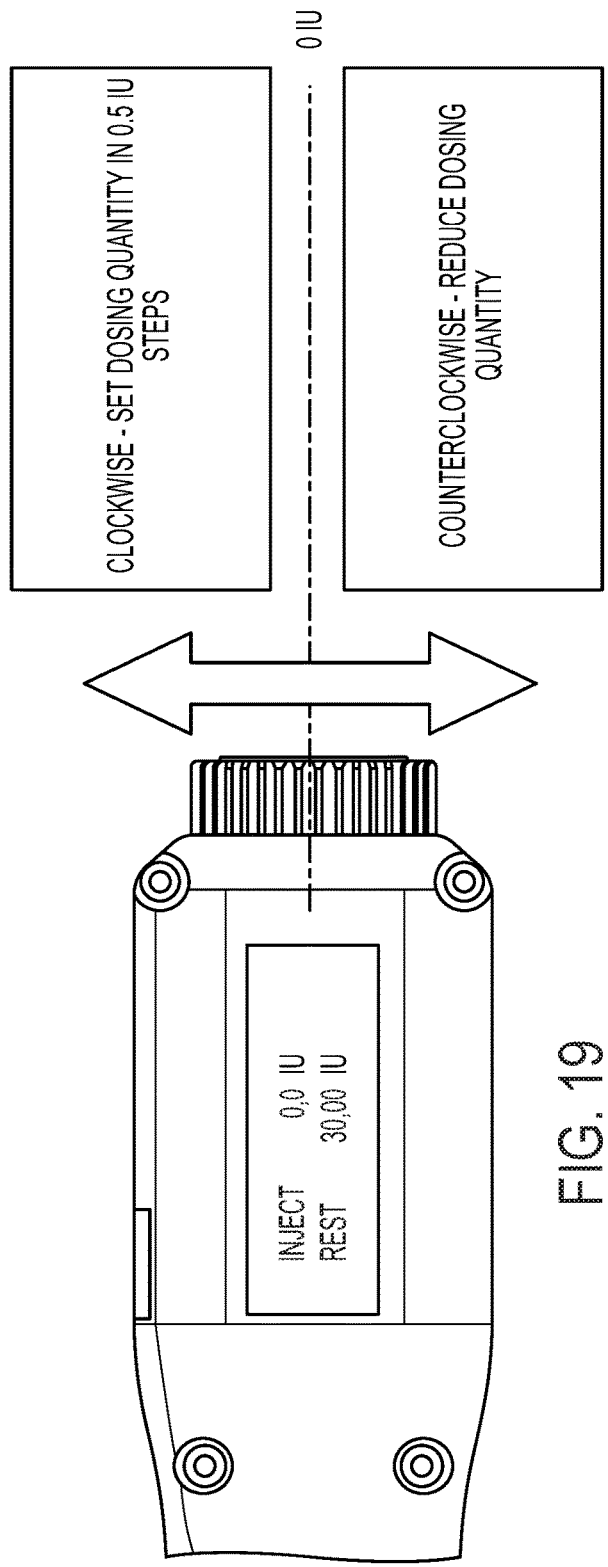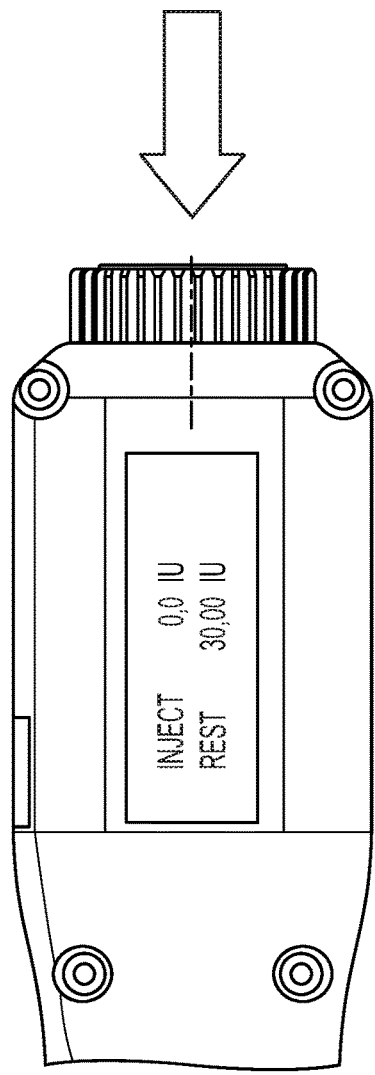

ⓘ PRIME 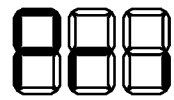
ⓘ REPLACE CARTRIDGE 
ⓘ RECENT INJECTED DOSE (e.g. 20 IU) 
ⓘ TIME SINCE LAST INJECTION (e.g. 220 min) 
ⓘ REMAINING UNITS (e.g. 220) 
ⓘ UNITS SET (e.g. 60) 
ⓘ ERROR 
ⓘ BATTERY LOW (RECHARGE?) 
FIG. 23

ELECTRONIC INJECTOR FOR INJECTING A MEDICINAL PRODUCT

CROSS REFERENCE TO RELATED APPLICATION

The present disclosure claims priority to U.S. provisional patent application 62/564,531, filed on Sep. 28, 2017, the entire contents of which are herein incorporated by reference.

FIELD

The present disclosure relates generally to an electronic injector device, and more particularly, to an injector of the kind that provides for administration by injection of medicinal products from a multi-dose cartridge.

BACKGROUND

An injector may allow a user to set a dosage amount of a medicinal product. Such injectors have application where regular injection by persons without formal medical training occurs. This may be useful with persons having diabetes where self-treatment enables such persons to conduct effective management of their diabetes.

One example type of injectors includes pen-type injectors. Pen-type injectors generally then should be robust in construction and easy to use both in terms of physically operating the injector and understanding how to operate the injector. Furthermore, the injector may be manufactured to be disposable rather than reusable, and thus, the injector should be easy to dispose of such as suitable for recycling.

Moreover, the injector should be capable of delivering precise amounts of the medicinal product as needed. Therefore, it would be desirable to provide device(s) and method(s) to satisfy such requirements, and to implement an injector using electronics for enabling further robust functionality.

SUMMARY

In an example, an injector is described that includes a rotary knob for selecting a function of the injector and setting a dosing quantity for an injection, a button located on an end of the rotary knob for initiating the injection, an electric motor providing an output rotary motion, an encoder for evaluating the output rotary motion of the motor, and a processor coupled to the rotary knob, the button, the electric motor, and the encoder. The processor receives the selected function of the injector and the dosing quantity for the injection from the rotary knob and receives a signal from the button for initiating the injection and converts the dosing quantity into a number of encoder pulses. The processor controls operation of the motor based on the number of encoder pulses when dosage is triggered via receipt of the signal from the button for initiating the injection. The injector also includes a transmission coupled to the electric motor to convert a speed of the motor, and a threaded spindle coupled to the transmission that moves linearly based on the output rotary motion of the motor at the speed as converted by the transmission. The injector may also include a punch connected to an end of the threaded spindle, wherein linear movement of the spindle causes the punch to release medicament.

In another example, an injector is described that includes a spindle. The spindle includes a gear wheel, an internal spindle coupled to the gear wheel that is threaded along a length of the internal spindle, and an inner sleeve that includes internal threads for mating with threads of the internal spindle for positioning the internal spindle into the inner sleeve. The inner sleeve includes external threads as well. The spindle also includes a spindle nut that includes internal threads for mating with the external threads of the inner sleeve for positioning the inner sleeve into the spindle nut, and an outer sleeve into which the spindle nut, the inner sleeve, and the internal spindle are positioned in a retracted state. The outer sleeve includes an anti-rotation component, and rotation of the gear wheel in a first direction causes extension of the spindle by: extending the spindle nut away from the outer sleeve until the spindle nut meets an end of the inner sleeve via rotation of the internal spindle and the inner sleeve, and then extending the inner sleeve away from the internal spindle, thereby pushing the spindle nut and the outer sleeve forward.

In another example, a rotary knob for an injector is described that includes an outer housing rotatable for selecting a function of the injector and setting a dosing quantity for an injection, a button located internal to the outer housing that is actuatable for initiating the injection, and a light ring positioned within the outer housing and circumferential to the button. The light ring is illuminated in a sequence of illumination to inform of a status of the injection.

In still another example, an injector is described that includes a tactile dose-setting field for receiving a sliding contact input to set a dosing quantity for an injection, and the tactile dose-setting field includes a display area for indicating the dosing quantity with graphical indicators. In this example, the injector also includes a tactile component coupled to the tactile dose-setting field for providing force, motion, or vibration feedback based on receipt of the sliding contact at the tactile dose-setting field, and a dose indicator display coupled to the tactile dose-setting field for displaying the dosing quantity based on the sliding contact input.

In yet another example, an injector is described that includes a rotary knob having an outer housing rotatable for selecting a function of the injector and setting a dosing quantity for an injection, a button located on an end of the rotary knob and internal to the outer housing for initiating the injection, and a light ring positioned within the outer housing and circumferential to the button. The light ring is illuminated in a sequence of illumination to inform of a status of the injection. In this example, the pen-type injector also includes an electric motor providing an output rotary motion, an encoder for evaluating the output rotary motion of the motor, and a processor coupled to the rotary knob, the button, the electric motor, and the encoder. The processor receives the selected function of the injector and the dosing quantity for the injection from the rotary knob and receives a signal from the button for initiating the injection and converts the dosing quantity into a number of encoder pulses. The processor controls operation of the motor based on the number of encoder pulses when dosage is triggered via receipt of the signal from the button for initiating the injection. In this example, the pen-type injector also includes a transmission coupled to the electric motor to convert a speed of the motor, and a threaded spindle coupled to the transmission that moves linearly based on the output rotary motion of the motor at the speed as converted by the transmission. The threaded spindle includes a gear wheel, an internal spindle coupled to the gear wheel that is threaded along a length of the internal spindle, an inner sleeve that includes internal threads for mating with threads of the internal spindle for positioning the internal spindle into the inner sleeve and the inner sleeve includes external threads, a spindle nut that includes internal threads for mating with the external threads of the inner sleeve for positioning the inner sleeve into the spindle nut, and an outer sleeve into which the spindle nut, the inner sleeve, and the internal spindle are positioned in a retracted state. The outer sleeve includes an anti-rotation component, and rotation of the gear wheel in a first direction causes extension of the spindle by extending the spindle nut away from the outer sleeve until the spindle nut meets an end of the inner sleeve via rotation of the internal spindle and the inner sleeve, and then extending the inner sleeve away from the internal spindle, thereby pushing the spindle nut and outer sleeve forward. In this example, the pen-type injector also includes a punch connected to an end of the threaded spindle, and linear movement of the spindle causes the punch to release the medicament.

In yet a further example, an injector is described that comprises a rotary knob rotatable for selecting a function of the injector and setting a dosing quantity for an injection, and a light ring positioned within an outer housing of the rotary knob. The light ring is illuminated in a sequence of illumination to inform of a status of the injection.

In yet a further example, an injector is described that comprises a motor, whereby rotation of the motor causes a medicinal product to be expelled, and a button, which is pressed to initiate and maintain an injection of the medicinal product, whereby pressure applied to the button during the injection changes a speed of the motor and as such a speed of the injection.

In further examples, methods of use are described. One example method includes a method of operating an injector for an injection procedure. Another example method includes a method of operating an injector in an information mode. Another example method includes a method of operating an injector in a dose-setting and injection mode. Another example method includes a method of operating an injector in an injection completion mode. Still another example method includes a method of operating an injector in a cartridge replacement/reset mode.

In a specific example, a method for operating a spindle for an injector is described. The spindle comprises a gear wheel, an internal spindle coupled to the gear wheel that is threaded along a length of the internal spindle, an inner sleeve including internal threads for mating with threads of the internal spindle for positioning the internal spindle into the inner sleeve, a spindle nut including internal threads for mating with external threads of the inner sleeve for positioning the inner sleeve into the spindle nut, and an outer sleeve into which the spindle nut, the inner sleeve, and the internal spindle are positioned in a retracted state. The method comprises rotating the gear wheel in a first direction to cause extension of the spindle by extending the spindle nut away from the outer sleeve until the spindle nut meets an end of the inner sleeve via rotation of the internal spindle and the inner sleeve; and then extending the inner sleeve away from the internal spindle, thereby pushing the spindle nut and the outer sleeve forward.

In another example, a method for operating a rotary knob for an injector is described. The method comprises receiving a selection of a function of the injector via rotation of an outer housing of the rotary knob, setting a dosing quantity for an injection based on an amount of rotation of the outer housing, initiating the injection via actuation of a button located internal to the outer housing, and illuminating a light ring in a sequence of illumination to inform of a status of the injection. The light ring is positioned within the outer housing and circumferential to the button.

In another example, a method for operating an injector is described that comprises receiving an input for initiating a medicinal product to be expelled from the injector based on actuation of a button of the injector, based on detection of a continuous actuation of the button, maintaining administering of the medicinal product, based on detection of an interruption of the continuous actuation of the button, pausing administering of the medicinal product, and controlling a speed of a motor of the injector and as such a speed of injection based on a pressure applied to the button.

In another example, a method for operating an injector is described comprising receiving, via a tactile dose-setting field, a sliding contact input to set a dosing quantity for an injection. The tactile dose-setting field includes a display area for indicating the dosing quantity with graphical indicators. The method also comprises displaying, via a dose indicator display coupled to the tactile dose-setting field, the dosing quantity based on the sliding contact input.

The features, functions, and advantages that have been discussed can be achieved independently in various examples or may be combined in yet other examples further details of which can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 19 illustrates an example of the control component and operation of the rotary knob to select the dosing quantity, according to an example implementation.

FIG. 20 illustrates an example of the control component and operation of the button, according to an example implementation.

FIG. 23 is an illustration of example digital display characters, according to an example implementation.

DETAILED DESCRIPTION

Figure 1:
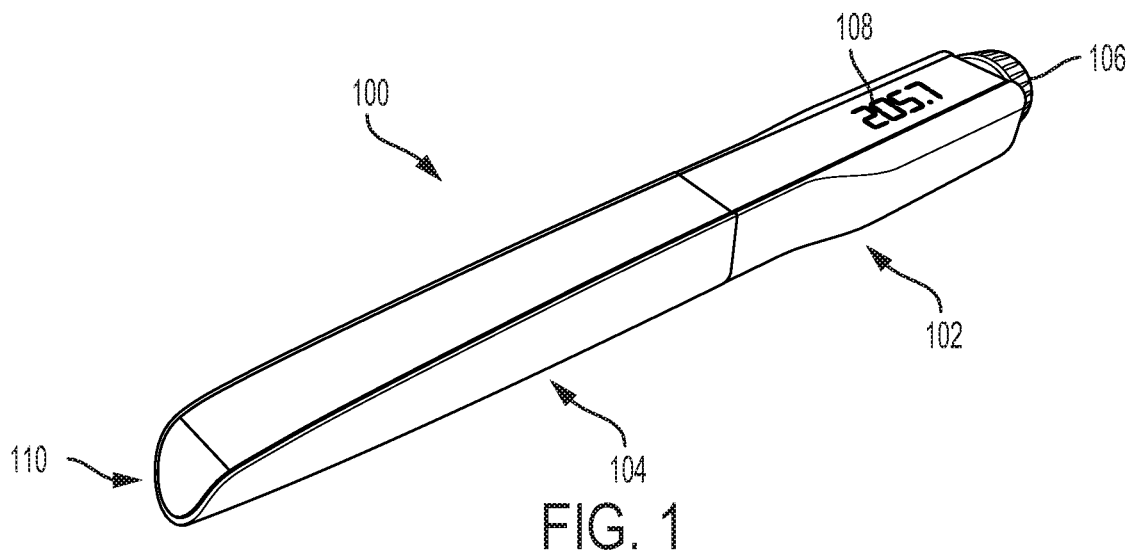
FIG. 1 illustrates an example injector, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Within examples described herein, an injector is described that includes a rotary knob for selecting a function of the injector and setting a dosing quantity for an injection and a button located on an end of the rotary knob for initiating the injection. The injector includes an electric motor providing an output rotary motion, an encoder for evaluating the output rotary motion of the motor, and a processor coupled to the rotary knob, the button, the electric motor, and the encoder. The processor receives the selected function of the injector and the dosing quantity for the injection from the rotary knob and receives a signal from the button for initiating the injection and converts the dosing quantity into a number of encoder pulses. The processor controls operation of the motor based on the number of encoder pulses when dosage is triggered via receipt of the signal from the button for initiating the injection. The injector includes a transmission coupled to the electric motor to convert a speed of the motor, a threaded spindle coupled to the transmission that moves linearly based on the output rotary motion of the motor at the speed as converted by the transmission, and a punch connected to an end of the threaded spindle, wherein linear movement of the spindle causes the punch to release the medicament.

In further examples, the spindle includes a gear wheel, an internal spindle coupled to the gear wheel that is threaded along a length of the internal spindle, an inner sleeve with internal threads for mating with threads of the internal spindle for positioning the internal spindle into the inner sleeve, a spindle nut with internal threads for mating with the external threads of the inner sleeve for positioning the inner sleeve into the spindle nut, and an outer sleeve into which the spindle nut, the inner sleeve, and the internal spindle are positioned in a retracted state. Rotation of the gear wheel in a first direction causes extension of the spindle by extending the spindle nut away from the outer sleeve until the spindle nut meets an end of the inner sleeve via rotation of the internal spindle and the inner sleeve, and then extending the inner sleeve away from the internal spindle, thereby pushing the spindle nut and outer sleeve forward.

In yet further examples, the rotary knob includes an outer housing rotatable (e.g., the rotary knob is rotatable as a whole) for selecting a function of the injector and setting a dosing quantity for an injection, a button located internal to the outer housing that is actuatable for initiating the injection, and a light ring positioned within the outer housing and circumferential to the button. In some examples, using the rotary knob for selecting functions is more intuitive to users of mechanical pens in contrast to use of buttons. The light ring is illuminated in a sequence of illumination to inform of a status of the injection.

In still further examples, the injector includes a tactile dose-setting field (in addition to or alternatively from the rotary knob, for example) for receiving a sliding contact input to set a dosing quantity for an injection, a tactile component coupled to the tactile dose-setting field for providing force, motion, or vibration feedback based on receipt of the sliding contact at the tactile dose-setting field, and a dose indicator display coupled to the tactile dose-setting field for displaying the dosing quantity based on the sliding contact input.

Figure 2:
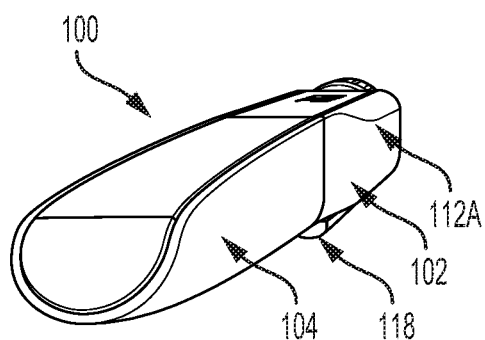
FIG. 2 illustrates a right side diagonal view along an end of the injector, according to an example implementation.
Figure 3:
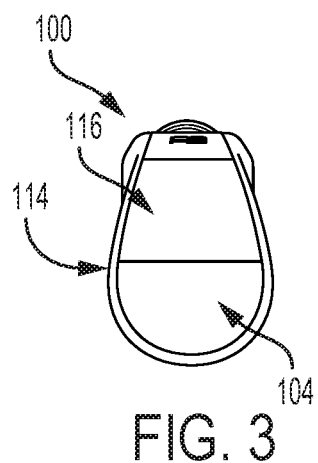
FIG. 3 illustrates a view along an end of the injector, according to an example implementation.
Figure 4:
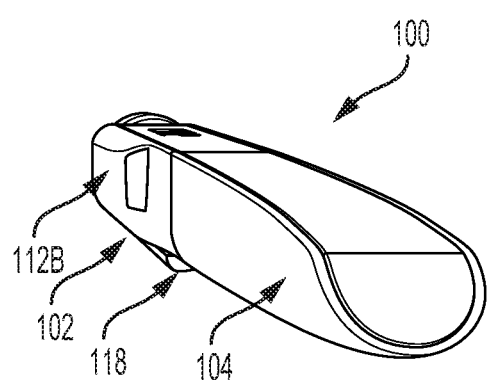
FIG. 4 illustrates a left side diagonal view along an end of the injector, according to an example implementation.

Referring now to the figures, FIG. 1 illustrates an example injector 100, according to an example implementation. FIG. 2 illustrates a right side diagonal view along an end of the injector 100, FIG. 3 illustrates a view along an end of the injector 100, and FIG. 4 illustrates a left side diagonal view along an end of the injector 100, according to example implementations.

The injector 100 includes a control component 102 and a cap 104. The control component 102 includes a control wheel 106 at an end and a display 108, and the control component 102 houses mechanical and electrical components of the injector 100.

As shown in FIGS. 1-4, the injector 100 may take the form of a pen-type injector, for example, having a shape and design similar to a pen or writing device. A pen-type injector may be more convenient and easier to transport than a traditional vial and syringe type injection device, and can be configured to provide repeatedly more accurate dosages. A pen-type injector may also be easier to use for those with visual or fine motor skill impairments. However, aspects of examples described herein are not limited to a specific pen-type injector, but rather are applicable to any number or type of injection devices or drug delivery systems.

As shown in FIGS. 1-4, the control component 102 and the cap 104 operate as sections of a housing for the injector 100. The display 108 is coupled to the control component 102 housing section, which has a back and two side portions, and the display 108 is coupled to the two side portions to enclose the control component 102 housing section. In this example, the display 108 is merged with an outer body of the injector 100, and can be completely integrated into the body of the injector 100. For example, a surface of the display 108 is shown to be an embedded window of the body of the injector 100. The display 108 may be a digital display, as described more fully below.

The cap 104 includes a tapered tip 110.

FIGS. 2 and 4 illustrate that the control component 102 has a width that decreases from the control wheel 106 to the cap 104. For example, the control component 102 includes protrusions 112a-b on sides of the control component 102.

FIG. 3 illustrates sides of the cap 104 have uniform smoothness and thickness, and sides and a back of the cap 104 and of the control component 102, respectively, are an integral (single) component 114, while a top 116 of each of the cap 104 and the control component 102 are a separate component. For example, the top of the control component 102 may be or include the display 108 merged into the control component 102.

FIG. 3 also illustrates that the control component 102 and the cap 104 are U-shaped, for example. The injector 100 has a shape with an anti-roll feature, for example, the shape is not round but rather has a U-shape. The control component 102 and the cap 104 couple together by snapping together to appear as an integral unit. The control component 102 and the cap 104 may comprise lightweight materials, such as plastic or aluminum.

The injector 100 also can include a clip 118.

Figure 5:
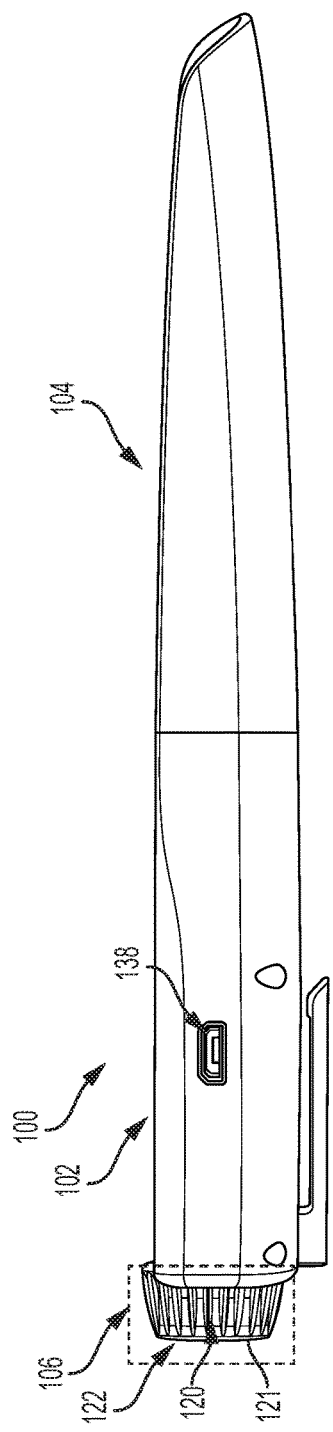
FIG. 5 is a side view of the injector, according to an example implementation.
Figure 6A:
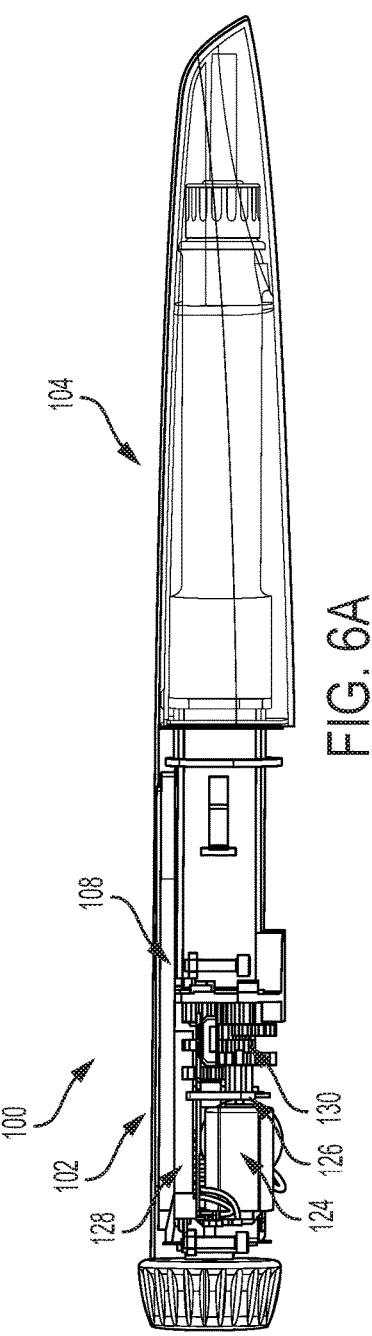
FIG. 6A is a transparent side view of the injector, according to an example implementation.
Figure 6B:
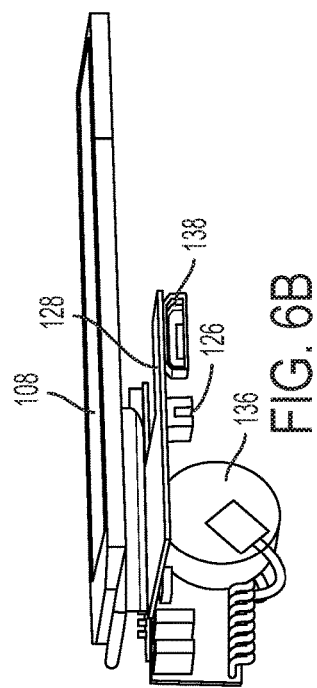
FIG. 6B is a magnified view of a portion of the injector, according to an example implementation.
Figure 7:
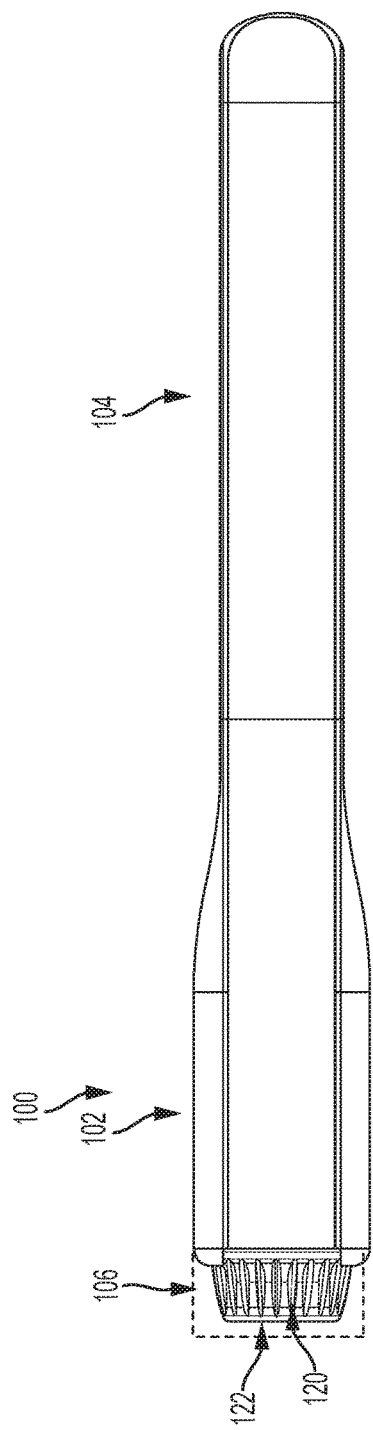
FIG. 7 is a top view of the injector, according to an example implementation.
Figure 8A:
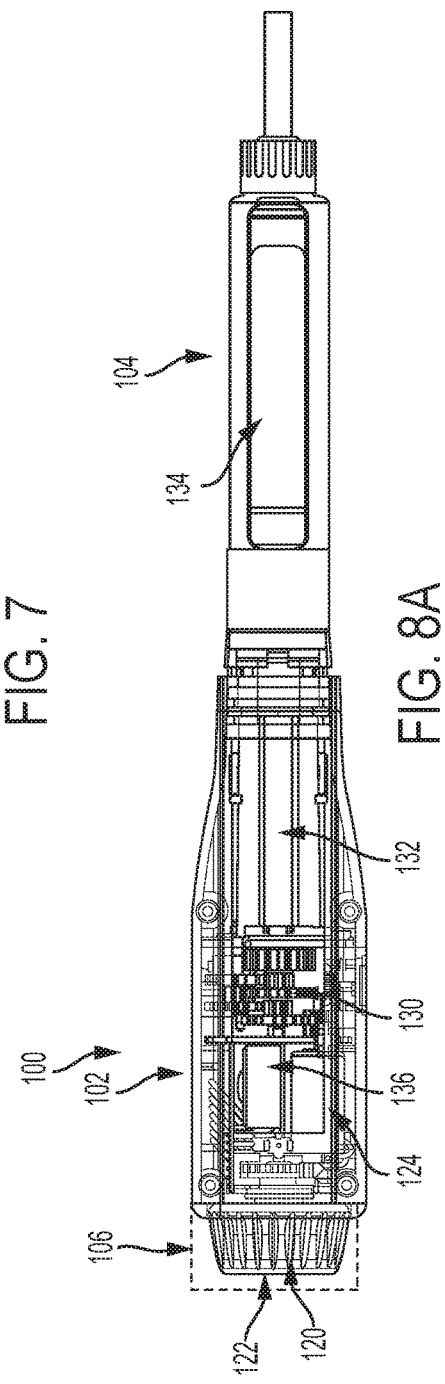
FIG. 8A is a transparent top view of the injector, according to an example implementation.
Figure 8B:
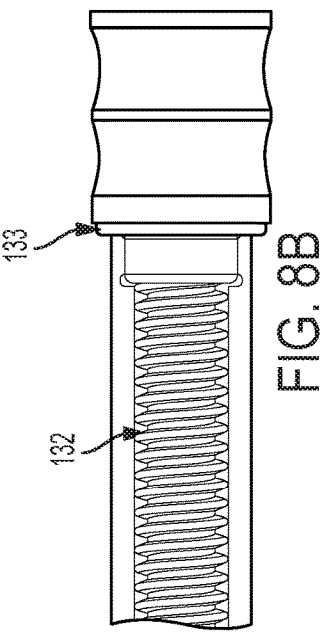
FIG. 8B is a magnified view of a portion of the injector, according to an example implementation.

FIG. 5 is a side view of the injector 100, according to an example implementation, and FIG. 6A is a transparent side view of the injector 100, according to an example implementation, and FIG. 6B is a magnified view of a portion of the injector 100, according to an example implementation. FIG. 7 is a top view of the injector 100, according to an example implementation, FIG. 8A is a transparent top view of the injector 100, according to an example implementation, and FIG. 8B is a magnified view of a portion of the injector 100, according to an example implementation.

The injector 100 includes the control wheel 106 with a rotary knob 120 for selecting a function of the injector 100 and setting a dosing quantity for an injection and a button 122 located on an end of the rotary knob 120 for initiating the injection. The injector 100 also includes an electric motor 124 providing an output rotary motion, an encoder 126 for evaluating the output rotary motion of the motor 124, and a processor 128 coupled to the rotary knob 120, the button 122, the electric motor 124, and the encoder 126.

The injector 100 also includes a transmission 130 coupled to the electric motor 124 to convert a speed of the motor 124, and a threaded spindle 132 coupled to the transmission 130 that moves linearly based on the output rotary motion of the motor 124 at the speed as converted by the transmission 130. In one example, the transmission 130 is a multi-stage spur gear.

The injector 100 also includes a punch 133 (shown in FIG. 8B) connected to an end of the threaded spindle 132. Linear movement of the spindle 132 causes the punch 133 to release medicament 134. In other examples, the punch 133 is not included as the spindle 132 can directly touch the stopper 170 of the cartridge to expel the drug.

The injector 100 further includes a battery 136 coupled to the motor 124 and the processor 128 to provide power. A universal serial bus (USB) interface 138 is further included on the pen-type injector coupled to the battery 136 to charge the battery, and coupled to the processor 128 to enable data communication to and from the injector 100.

Within examples, the processor 128 receives the selected function of the injector and the dosing quantity for the injection from the rotary knob 120 and receives a signal from the button 122 for initiating the injection and converts the dosing quantity into a number of encoder pulses. For example, a user rotates the rotary knob 120 to change or input a dosing quantity, and then the user pushes the button 122 to initiate the injection. Turning the rotary knob 120 may be intuitive to a user, and turning the rotary knob 120 is faster than pressing buttons a number of times to input a specific dosage (as with other pen injector designs). Rotation of the rotary knob 120 clockwise (or in a first direction) is performed to set a dose (and there may or may not be a maximum dose setting allowed). Rotation of the rotary knob 120 counterclockwise (or in a second direction opposite the first direction) enables a dose correction (e.g., decrease a dose).

Pushing the button 122 is a mechanical process to enable a user to provide input to the processor 128. The button 122 may have a two-step push depth with different actions/features enabled via spring elements in the button 122. For example, pushing the button 122 to a first depth can trigger display of quantities or a menu for actions on the display 108, and pushing the button 122 to a second depth more than the first depth can trigger a signal to be sent to the processor 128 to initiate the dose.

A continuous press of the button 122 to the second depth can cause injection to initiate and continue until completion of the dosage. The injector 100 may be configured such that an interruption of the continuous press causes the injection to pause, for example.

In some examples, the injector 100 can be configured to be in a continuous press mode or a binary press mode to operate the injector 100. For example, a user may input a selection of a specific mode through operation of the button 122. Following, for operation of the injector 100 in continuous press mode, a continuous press of the button 122 to a predetermined depth may be required. Or, for operation of the injector 100 in the binary press mode, a sequence of press the button 122 once to start the injection, press the button 122 again to stop/pause the injection, press the button 122 again to start another injection, etc., can be followed. Thus, in the binary press mode, the button, when pressed a first time, initiates the injection, and when pressed a second subsequent time, stops the injection.

The button 122 may further include a touch-sensitive surface 121 (e.g., on a top of the button as the surface pushed inward by the user). The touch-sensitive surface 121 may operate using a capacitive touch-sensitive surface to receive an input based on a touch-contact due to the pressing force by a user. The touch-contact can be programmed to provide an input for a control mechanism of the injector 100, such as to cause an injection to trigger, cause the injection to continue (e.g., through continuous press detection), modify a dose setting, etc. The touch-sensitive surface 121 may further include a fingerprint sensor such that the injector 100 requires an authentication for use.

In addition, the button 122 may include other or additional integrated sensors (other than or in addition to a fingerprint sensor), such as a proximity sensor (e.g., programmed to wake-up or light up the display 108 based on detection of an object in proximity, such as when a user picks up the injector 100 and hovers their finger over the button 122), an accelerometer/gyroscope or inertial measurement unit (IMU) to detect an orientation of the injector 100 and control orientation of items on the display 108, or other sensors as well.

The button 122 may be capable to provide haptic feedback, and thus, may include a vibration component. In addition, the button 122 may be capable to provide visual feedback, and thus, may include a display in place of the touch-sensitive surface 121. Or, the touch-sensitive surface 121 may be a touch-sensitive display.

The processor 128 then controls operation of the motor 124 based on the number of encoder pulses (e.g., due to rotation of the rotary knob 120) when dosage is triggered via receipt of the signal from the button 122 for initiating the injection. For example, the processor 128 can control power provided to the motor 124 so that no power is provided to disable the motor 124, and power is provided for a duration long enough to achieve the number of rotations of a shaft of the motor 124 as indicated by the number of encoder pulses.

The injector 100 and/or the processor 128 can further include memory to store instructions that when executed by the processor 128, causes the processor 128 to control operation of the motor 124. The memory also may store values including an injection history, a punch position, and user values, for example.

As mentioned, the control component 102 and the cap 104 operate as sections of a housing for the injector 100. The electric motor 124, the encoder 126, the processor 128, the transmission 130, and the threaded spindle 132 are all included within the control component 102 housing section.

Figure 9:
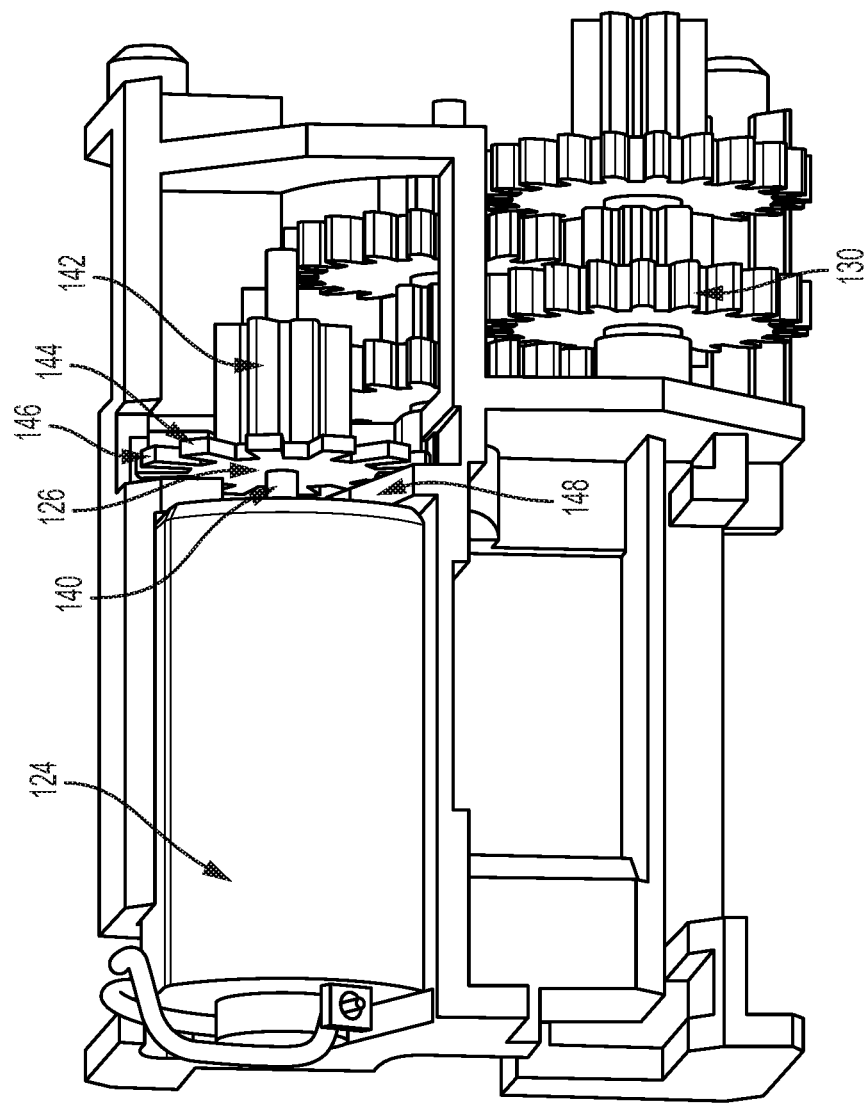
FIG. 9 illustrates a portion of mechanical components of the injector, according to an example implementation.

FIG. 9 illustrates a portion of mechanical components of the injector 100, according to an example implementation. For example, FIG. 9 illustrates the motor 124 having a shaft 140 that is coupled to the encoder 126. The encoder 126 couples to the transmission 130 through a pinion 142. The encoder 126 includes an encoder disk 144 with segmented windows 146 that is positioned on the shaft 140 of the motor 124, and a fork light barrier 148. Rotary motion of the motor 124 is evaluated and monitored by the encoder 126, which has the encoder disk 144 sitting directly on the shaft 140 of the motor 124. Due to the gear ratio and the spindle pitch, a very high resolution of the encoder steps is achieved with respect to a distance traveled by the punch. With the high resolution, a high accuracy is achieved in positioning and thus in the dosing of the medicament.

Gearing of the transmission 130 requires no lubrication, and is made of lightweight elements. Further, the transmission 130 is a high-speed transmission that consumes low amounts of energy.

The processor 128 converts the adjusted dosing quantity into a number of necessary encoder pulses. The parameters for the conversion include encoder resolution, gear ratio, spindle pitch and carpule diameter. An example calculation to convert the adjusted dosing quantity into a number of encoder pulses includes using an encoder with a resolution of 12 ticks per rotation, and a gear box with five levels of a gearing ratio 22/7 each, leading to an overall gearing ratio of 306.636, and a pitch of the spindle is 1 mm. Thus, the encoder 126 has a resolution of 3,679.6 ticks per millimeter movement of the spindle. The encoder 126 enables high precision for high dose accuracy, and produces little to no sound in use (e.g., silent gearwheel run).

A nominal inner diameter of the standard 3 ml cartridge is 9.65 mm, and thus, to expel a dose of 0.01 ml the rubber stopper has to be pushed by 0.1367 mm. The encoder has a resolution of about 503.1 ticks per 0.01 ml. Examples can include more than 503.1 ticks per 0.01 ml (e.g., 505.9).

In insulin, a typical concentration is 100 IU/ml. The injector 100 can set the target dose in steps (increments) of 1 IU (0.01 ml), if the standard 3 ml cartridge and 100 IU/ml insulin are used. In such examples, the encoder 126 has a resolution of about 503.1 ticks per 1 IU. In other examples, the injector 100 can set the target dose in increments of 0.5 IU (0.005 ml), and in such examples, the encoder 126 has a resolution of about 251.6 ticks per 0.5 IU.

For small doses, a dose accuracy of the injector 100 should be the incremented, such as by setting in increments of 0.005 ml to, say, 0.045 ml, and the expelled dose can be 0.045 ml±0.005 ml. For an injection speed of 0.10 ml/s (10 IU/s), the motor 124 may be operated at about 419 rotations per second or 25,155 rotations per minute.

When the dosage is triggered, the processor 128 controls the motor 124 so that the motor 124 stops after reaching the calculated number of encoder steps. By adapting the parameters, the injector 100 can be configured at the factory to be used for different carpule diameters.

Figure 10:
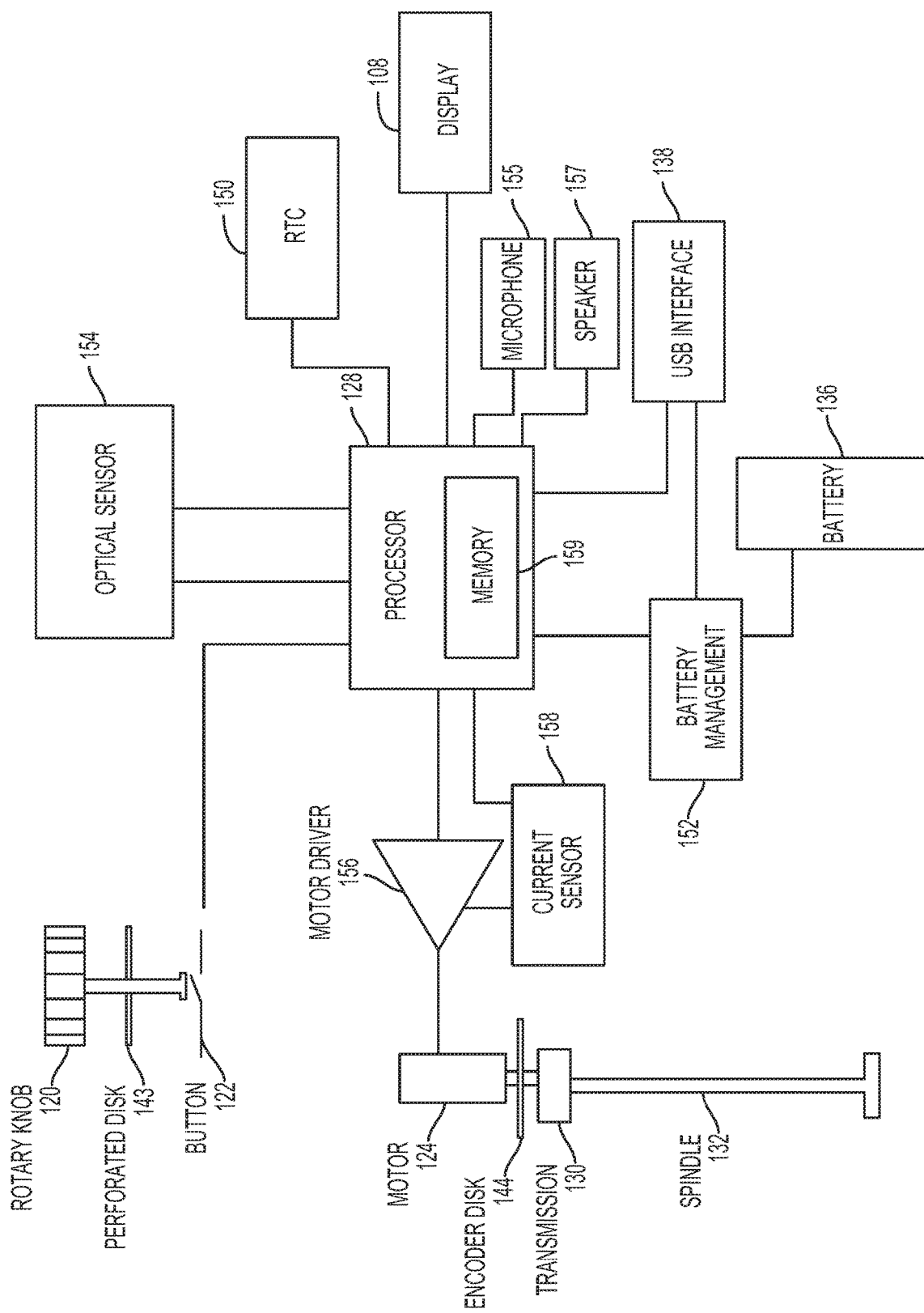
FIG. 10 is a block diagram illustrating example electronic and mechanical components of the injector, according to an example implementation.

FIG. 10 is a block diagram illustrating example electronic and mechanical components of the injector 100, according to an example implementation. The electronics include the processor 128 coupled to the button 122, the rotary knob 120, a real time clock (RTC) 150, the display 108, the USB interface 138, the battery 136 and battery management 152, optical sensor 154, and a motor driver 156 and a current sensor 158 for driving the motor 124, as well as a microphone 155 and a speaker 157.

The processor 128 may be a general-purpose processor or a special purpose processor (e.g., digital signal processors, application specific integrated circuits, etc.). Although only one processor is shown, more than one processor may be included in the injector 100. The processor 128 may receive inputs from the button 122, the rotary knob 120, the RTC 150, the USB interface 138, the battery management 152, the optical sensor 154, and the motor driver 156 and the current sensor 158, and process the inputs to generate outputs that are stored in memory and used for controlling operation of the motor 124. The processor 128 can be configured to execute the executable instructions (e.g., computer-readable program instructions) that are stored in the memory/data storage and are executable to provide the functionality of the injector 100 described herein.

The processor 128 may include an 8-bit microcontroller with a flash memory. A radio interface (Bluetooth) can be included as well. The processor 128 may further include integrated EEPROMs to store data such as the time and amount of the last injections, which are retained even when the battery is empty. An integrated A/D converter can also be used to manage the battery from this controller. Time functions such as countdown could be integrated, and a real-time clock may be implemented with an additional component. If required, a voltage conversion can be integrated on the printed circuit board. Electronics can be sealed to protect against moisture as well.

The processor 128 thus includes a memory 159 for storing set values (e.g., injection history, stamp position, set user values, etc.), and the executable instructions. The memory 159 may include or take the form of one or more computer-readable storage media that can be read or accessed by the processor 128. The computer-readable storage media can include volatile and/or non-volatile storage components, such as optical, magnetic, organic or other memory or disc storage, which can be integrated in whole or in part with the processor 128. In such an example, the memory 159 may be separate from the processor 128. The memory 159 is considered non-transitory computer readable media. In some examples, the memory 159 can be implemented using a single physical device (e.g., one optical, magnetic, organic or other memory or disc storage unit), while in other examples, the memory 159 can be implemented using two or more physical devices.

The memory 159 thus is a non-transitory computer readable storage medium, and executable instructions are stored thereon. The instructions include computer executable code. When the instructions are executed by the processor 128, the processor 128 is caused to perform functions.

The injector 100 includes two fork light barriers. For example, one fork light barrier is provided for evaluating the encoder disk 144, and a second is provided for evaluating the rotary knob 120, and may include a perforated disk 143. The button 122 is used to evaluate the operating key.

A clock can be displayed with the RTC 150. This can be used to implement various functions for which time is needed. Examples of functions with the clock include storing the injection history with time, reminding the user of the next injection, determining a holding time/waiting time after injection, determining a return stroke after injection, and determining speed control (e.g., express, start, and injection end).

The display 108 may be a digital display and depending on the function mode, different values can be displayed via the display 108. In some examples, the display 108 may be an organic light emitting diode (OLED) or a liquid crystal display (LCD).

The battery 136 is charged via the USB interface 138. In other examples, the battery 136 may be charged using conductive battery charging in addition to or alternatively than using the USB interface 138.

The USB interface 138 also enables a connection to a computer or computing device to receive and/or transmit data by the processor 128, such as, for example, to enable data sharing (e.g., ability to provide settings to the injector 100, download data indicating dosages administered, upload data indicating future dosage times/amounts, etc.). In other examples, data sharing may occur via wireless data transmission by including a Bluetooth or otherwise wireless receiver/transmitter within the injector 100, for instance, in addition to or alternatively than the USB interface 138.

Power is supplied by the battery 136. The battery management 152, which may be performed via execution of instructions by the processor 128, monitors a charge level of the battery 136 and the battery charge via the USB interface 138. The battery 136 may be a primary cell or a rechargeable battery based on a number of injections per day, the duration of an injection, the desired operating time without recharging or battery change, and the power consumption during operation. The battery 136 may be a zinc/coal, zinc/air, as well as alkaline and lithium type battery. Use of a rechargeable battery requires charging and battery management in the electronics. Charging can be performed via a mini or micro-USB socket, such as the USB interface 138. The battery may be a nickel metal hydride (NMH) type, such as a V40 H battery with a capacity of 40 mAh, or a comparable lithium battery with a capacity of 90 mAh. The battery 136 may be a cuboidal cell, round cells, and/or coin cell type. The battery 136 supplies the required current when the motor 124 is running under load, and an internal resistance of the battery 136 should not be too high and should not increase too much during discharge.

The motor 124 is controlled via motor driver 156 and the current sensor 158. With the fork light barrier and the encoder disk 144, a closed control circuit of the motor driver 156 can be built up. The motor 124 may be a permanently excited DC motor, and operation of the motor 124 can be realized with a full bridge control system that allows all operating modes, including braking. A speed control can be implemented as well, which receives the speed as feedback via a vane wheel with light barrier and controls the motor power via pulse width modulation. This allows for variable motor speed and sufficient torque even at low speeds. In addition, the voltage variation can be compensated during battery discharge. The control loop can be implemented and designed via the processor 128. The speed of the control loop would be sufficiently high and accurate in this case. The slowest element would be the motor itself, which with its mass inertia and maximum power can be a limiting factor. A photoelectric sensor system can be used for speed detection, as well as a magnetic field sensor (Hall sensor).

Motor current can be filtered to ensure that EMC emissions are within specifications. Low operating voltage and high integration of the controller results in a low problematic radiation on the PCB. The USB socket can be protected by a line filter on the printed circuit board.

The motor driver 156 and the current sensor 158 enable an auto-priming function (by motor current detection). Automatic priming may include the motor 124 automatically moving the spindle 132 to the stopper of the cartridge. An increase of motor current or its gradient when reaching the stopper can be used for shutdown. The compressed stopper can then be relieved by the motor 124 resetting a piece of the plug. This minimizes a loss of the medicament/drug due to dripping, for example.

To achieve dose accuracy of an injection, the piston rod (or spindle 132) is positioned into contact with the stopper of the cartridge already before the injection starts. But after exchanging the cartridge, the piston rod is brought to a correct position relative to the stopper before performing the first injection.

A user attaches a needle to the injector 100 and repeatedly sets a small dose and presses the button, until a flow of medicinal product is visible. The electronics detect the increase of the motor current when reaching the stopper. If the motor stops too early, the first dose is low. If the motor stops too late, the amount of liquid wasted during priming is high. Such a priming with a needle attached can also be used to expel air inside the cartridge.

The motor 124 could run back once the stopper is reached—building up some pressure and releasing it afterwards to avoid expelling unused medicinal product. When using a cartridge with low internal friction, the increase of the force when reaching the stopper may be low. A difference of the force between expelling air and expelling drug may be difficult to detect.

In some examples, priming can be performed with no needle attached. For example, priming is started by briefly pressing the button 122 with the spindle 132 in a reference position (e.g., using function, "go home", to have the piston travel back to the reference position). Then the function, "prime", is selected and executed. The plug of the carcass is detected at the primary by a current limit of the drive motor. When the piston reaches the stop, the moment of the drive motor is increased. The motor 124 draws more current, and the motor 124 switches off at an adjustable current value. After priming, the piston automatically performs a jerk stroke without waiting time. In this example, the motor 124 can run until the electronics detect the compression of the stopper. So in order not to stop too early, a high compression is accepted at first. But, after reaching that high compression, the motor 124 runs back to reduce the compression. As no needle is attached, the compression does not lead to expelling unused medicinal product.

In some examples, the piston rod is moved until a certain limit force is reached and then moved back by a certain distance. A correct limit force and correct distance are evaluated in tests and depend on properties of the cartridge.

If the automatic priming was done with the needle attached, an increase of force when initially reaching the stopper may be lower, and as such, may be difficult to distinguish from an uneven running.

FIG. 10 also illustrates the microphone 155 and the speaker 157 coupled to the processor 128. The microphone 155 can receive audio inputs, such as voice inputs or voice commands, for voice control of the injector 100. In some examples, for a voice command to be accepted by the processor 128, a further authentication may be required (e.g., authentication through the fingerprint sensor of the button 122). The speaker 157 operates to provide an audio output to the user, such as to confirm receipt of a command, or to indicate a status of the injection.

Some example voice commands for which the processor 128 may be programmed to receive include "When was the last time I injected myself?", "Is there enough drug in the cartridge to get the set dose?", "Is the injection over?", "What do I have to do with the empty cartridge?". The processor 128 operates to provide responses to the user through the speaker 157 by accessing the memory 159 for executable instructions.

Figure 11:
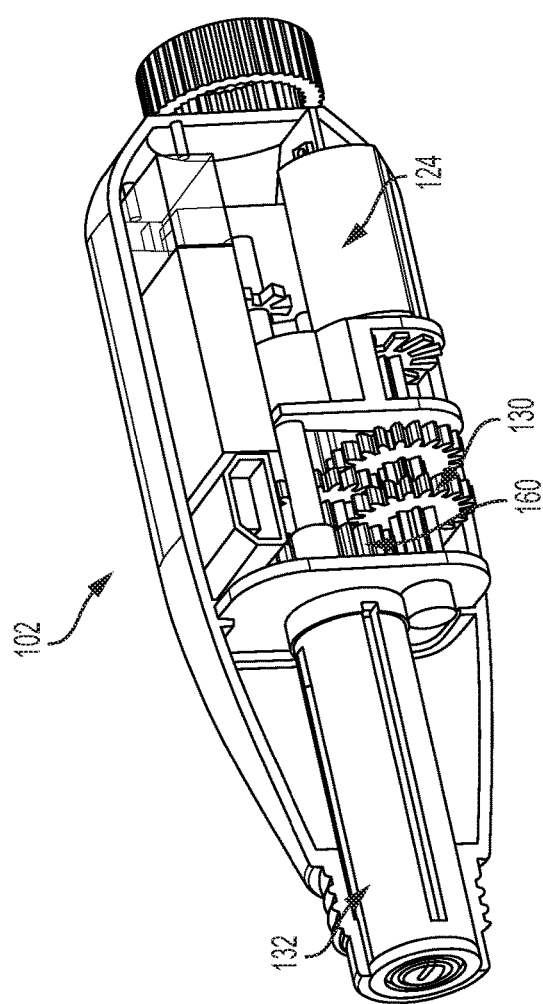
FIG. 11 illustrates the control component of the injector, according to an example implementation.
Figure 12:
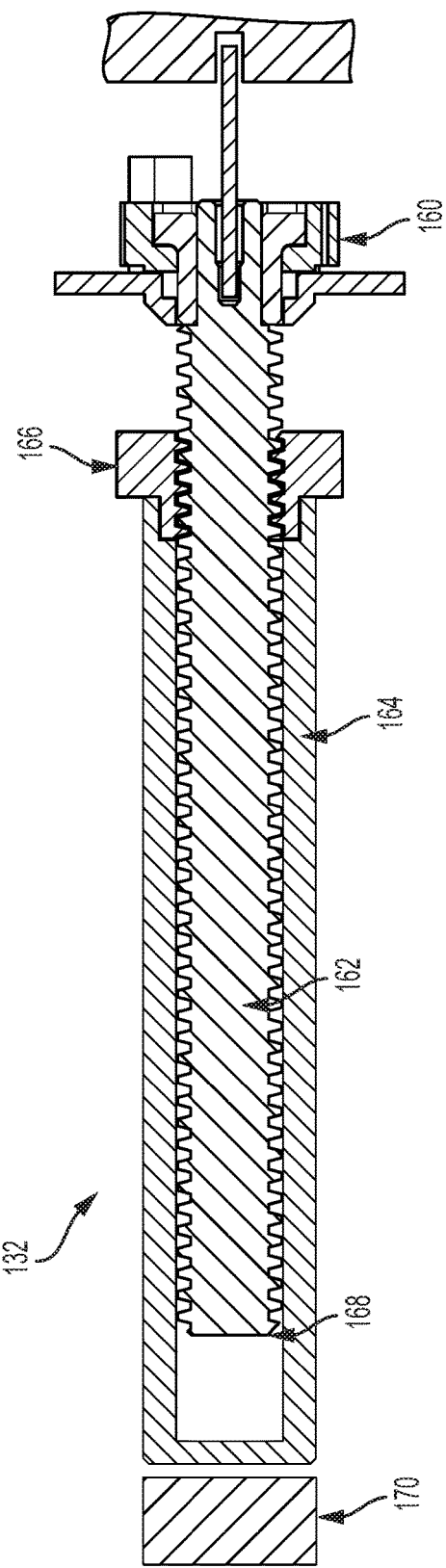
FIG. 12 illustrates an example of the spindle for the injector, according to an example implementation.

FIG. 11 illustrates the control component 102 of the pen-type injector, according to an example implementation, and FIG. 12 illustrates an example of the spindle 132 for the injector 100, according to an example implementation. The spindle 132 is driven via a gear wheel 160 that connects the spindle 132 to the transmission 130 and motor 124. Thus, operation of the motor 124 causes the transmission 130 to drive the gear wheel 160 for rotation of the gear wheel 160. And, the motor 124 may be operated, as described herein, via pressing of the button 122 and/or using the rotary knob 120.

In FIG. 12, the spindle 132 includes an internal spindle 162 coupled to the gear wheel 160, and the internal spindle 162 is threaded along a length of the internal spindle 162. The spindle 132 also includes a spindle nut 164 and a screw nut 166 with threads to mate with threads of the internal spindle 162. Rotation of the gear wheel 160 in a first direction causes extension of the spindle 162 outward forcing a stamp 168 to extend outward into the stopper 170.

Figure 13:
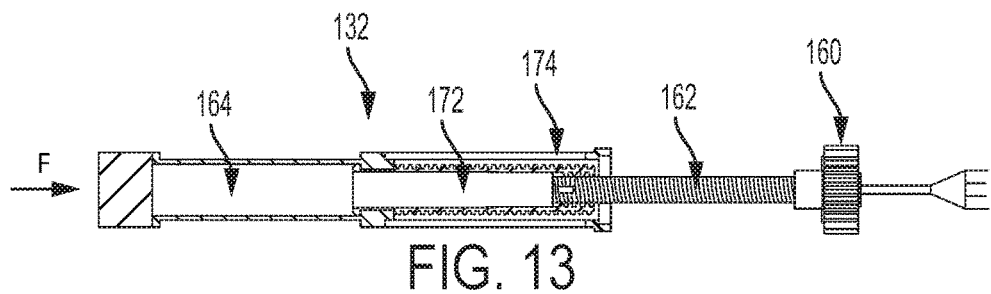
FIG. 13 illustrates a side view of the spindle fully extended, according to an example implementation.
Figure 14:
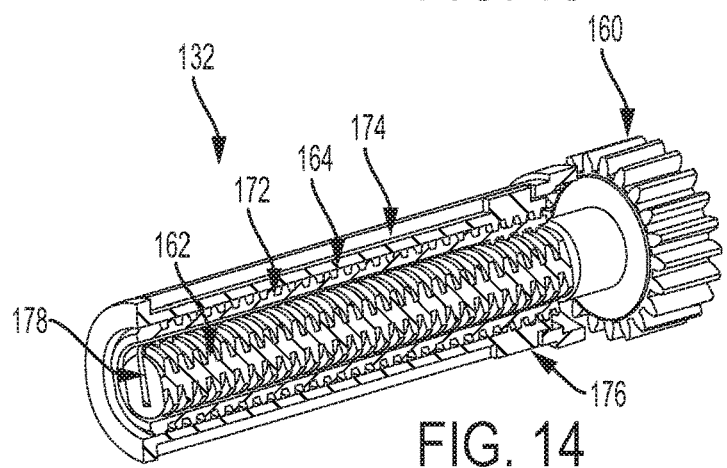
FIG. 14 illustrates a transverse view of the spindle fully retracted, according to an example implementation.
Figure 15:
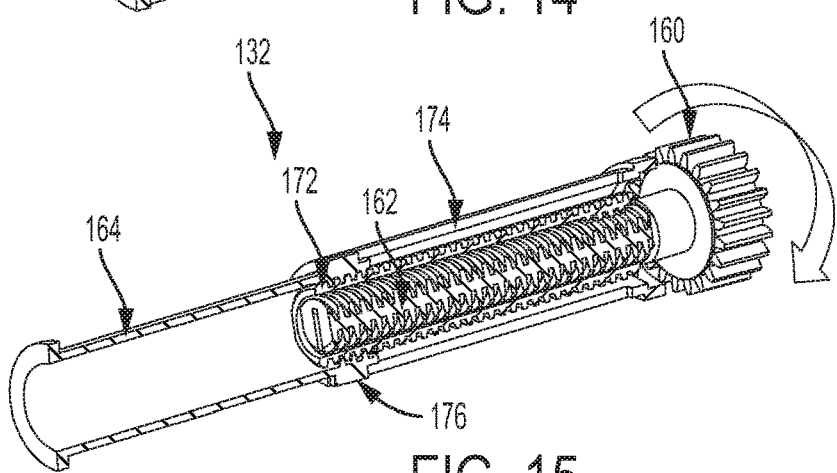
FIG. 15 illustrates a transverse view of the spindle partially extended, according to an example implementation.
Figure 16:
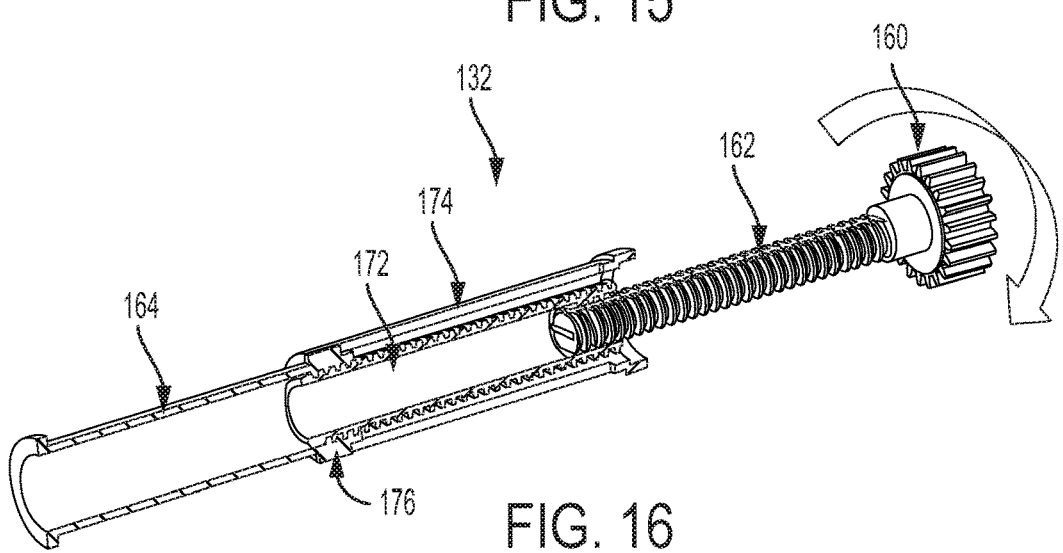
FIG. 16 illustrates a transverse view of the spindle fully extended, according to an example implementation.

FIGS. 13-16 illustrate another example of the spindle 132, according to an example implementation. In FIGS. 13-16, the spindle 132 is a telescoping spindle, for example. FIG. 13 illustrates a side view of the spindle 132 fully extended according to an example implementation, FIG. 14 illustrates a transverse view of the spindle 132 fully retracted according to an example implementation, FIG. 15 illustrates a transverse view of the spindle 132 partially extended according to an example implementation, and FIG. 16 illustrates a transverse view of the spindle 132 fully extended according to an example implementation.

The spindle 132 includes the gear wheel 160, and the internal spindle 162 coupled to the gear wheel 160. The internal spindle 162 is threaded along a length of the internal spindle 162 as shown. The spindle 132 also includes an inner sleeve 172 that includes internal threads for mating with threads of the internal spindle 162 for positioning the internal spindle 162 into the inner sleeve 172. The inner sleeve 172 also includes external threads.

The telescoping spindle 132 further includes the spindle nut 164, which includes internal threads for mating with the external threads of the inner sleeve 172 for positioning the inner sleeve 172 into the spindle nut 164. The telescoping spindle 132 further includes an outer sleeve 174 into which the spindle nut 164, the inner sleeve 172, and the internal spindle 162 are positioned in a retracted state, as shown in FIG. 14. The outer sleeve 174 also includes an anti-rotation component 176 that prevents the outer sleeve 174 from rotating with respect to the inner sleeve 172.

In operation, rotation of the gear wheel 160 in a first direction causes extension of the telescoping spindle 132 by extending the spindle nut 164 away from the outer sleeve 174 until the spindle nut 164 meets an end of the inner sleeve 172 via rotation of the internal spindle 162 and the inner sleeve 172, as shown in FIG. 15. Then, further rotation of the gear wheel 160 in the first direction causes extension of the inner sleeve 172 away from the internal spindle 162, thereby pushing the spindle nut 164 and the outer sleeve 174 forward, as shown in FIG. 16.

The telescopic spindle 132 has an advantage in that a length in the retracted state shortens. By driving the gear wheel 160, the inner sleeve 172 moves outwards against the internal spindle 162 and pushes the parts forward. The outer sleeve 174 thereby assumes the axial guidance and the anti-rotation component 176 relative to the housing section of the control component 102. A locking plate 178 positioned within an end of the internal spindle 162 prevents the internal spindle 162 from being unscrewed from the inner sleeve 172 and forms the end stop part to part.

Example operational sequence of the telescoping spindle 132 during the extension of the parts depends on an internal friction of the spindle 132. The inner sleeve 172 is freely rotatable except for the end stops. The spindle 132 may be retracted by rotation of the gear wheel 160 in a second direction that is reverse of the first direction (e.g., retraction of the spindle 132 in an inverse order of the extension).

Using the telescopic spindle 132 enables a length of the injector 100 to be shorter in comparison to other existing piston/rod-type injectors. In addition, when the telescopic spindle 132 is retracted, there is more space inside the injector 100 (as compared to existing piston/rod-type injectors) for electronic components. Furthermore, with existing piston/rod-type injectors, a maximum possible plunger-stroke is based on a length of the rod. However, using the telescopic spindle 132 enables varying a stroke length, as well as accomplishing the same plunger-stroke as with existing injectors but with a shorter spindle, for example.

Figure 18:
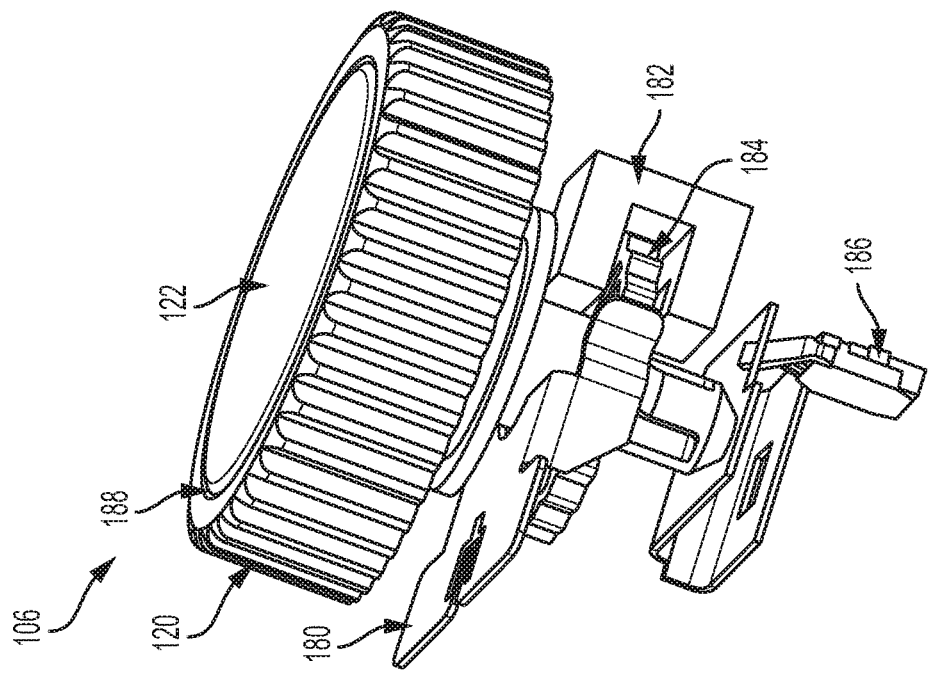
FIG. 18 illustrates an example of the control wheel, according to an example implementation.
Figure 17:
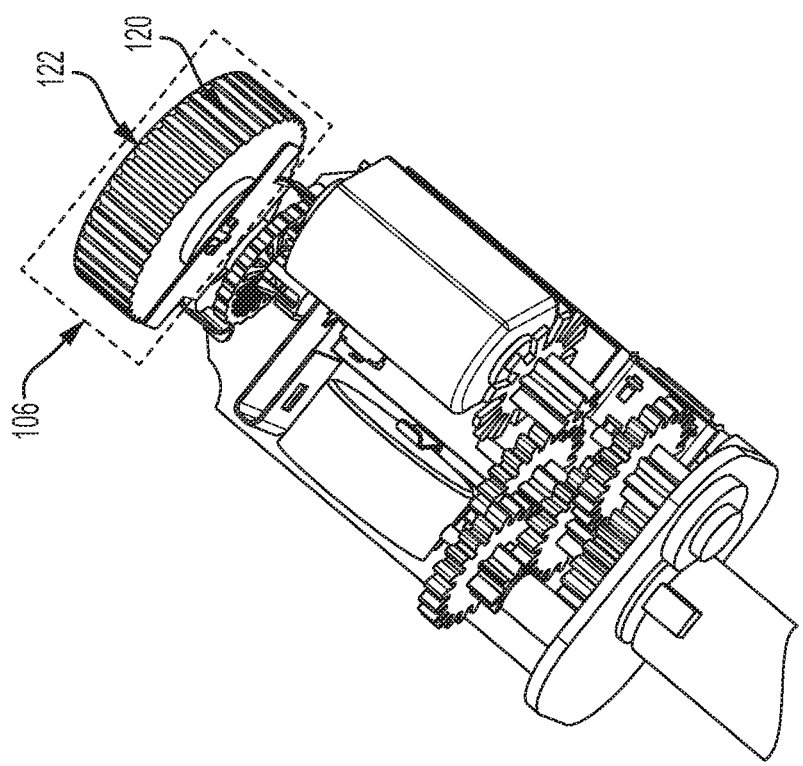
FIG. 17 illustrates another portion of the control component including the control wheel, according to an example implementation.

FIG. 17 illustrates another portion of the control component 102 including the control wheel 106, according to an example implementation. FIG. 18 illustrates an example of the control wheel 106, according to an example implementation.

As shown in FIG. 18, the control wheel 106 includes the rotary knob 120, which may be an outer housing rotatable for selecting a function of the injector 100 and setting a dosing quantity for an injection, and the button 122 located internal to the outer housing provided by the rotary knob 120 that is actuatable for initiating the injection.

In another example, the rotary knob 120 may not include a separate button 122, but rather, the rotary knob 120 is a single component that is actuatable for initiating the injection by being pressed into a body of the injector 100.

The rotary knob 120 is noticeable when turning (similar to a wheel of a computer mouse). The rotary knob 120 can be used to: a) select various functions and b) set the values, and the values can be saved or confirmed with the button 122. The rotary knob 120 can also be used to select function mode/menu, set the IU value, set other values (e.g., clock, language, etc.), and to select a lock function against unintentional switching on (for example, first press button, then turn). The menu may include a user interface listing possible actions or functionality of the injector 100, and the menu may be displayed on the display 108. For example, the menu may list a mode of the injector, and allow a user to scroll through possible modes and provide possible inputs for selection.

The processor 128 may provide the menu of functions and controls operation of the injector 100 based on the selected function of the injector 100 and the dosing quantity for the injection received from the rotary knob 122. The menu of functions can be stored in the memory 159, and accessed by the processor 128 to provide for selection via the rotary knob 122. In some examples, the processor 128 provides the menu of functions for display on the display 108 to enable the user to scroll through the possible functions in order to make a selection.

The button 122 can be used to set value, power off, and start injection of the set value.

Thus, within examples, the injector 100 may be operated using the control wheel 106, which can detect left and right rotation of the rotary knob 120 and also has a push-button function. This makes entering values more elegant and quicker than using several keys. The rotary knob 120 could be read in by another light barrier combined with a paddle-wheel. Switching the injector 100 on and off could also be performed by the rotary knob 120. For example, by twisting or rotating the rotary knob 120 in the pressed position, it could slip into a lock and initiate the switch-off by pressing the push-button function continuously. A retractable version would also be possible, so that the rotary knob could be used in the same way as a ballpoint pen is only locked by pressing.

In FIG. 18, the control wheel 106 is further shown to include a spring plate 180 for rotation, a light barrier 182, an encoder disc 184 for the light barrier, and a micro-switch 186 for push button control of the button 122. The spring plate 180, the light barrier 182, and the encoder disc 184 operate similar to the encoder 126 of the motor 124 (described above) so as to provide information to the processor 128 to enable determination of rotation of the rotary knob 120.

FIG. 19 illustrates an example of the control component 102 and operation of the rotary knob 120 to select the dosing quantity, according to an example implementation. For example, turning the rotary knob 120 clockwise can set the dosing quantity in 0.5 IU steps, as shown. Rotating counterclockwise can reduce the dosing quantity.

FIG. 20 illustrates an example of the control component 102 and operation of the button 122, according to an example implementation. For example, pressing the button 122 in the direction as shown by the arrow in FIG. 20 can cause different functionality to occur based on a duration of the press. For instance, a three (3) second press can result in powering on/off the pen-type injector, a continuous press can start and cause the injection to occur, and a single one (1) second press can cause selection/confirmation of a parameter selected via rotation of the rotary knob 120.

Referring back to FIG. 18, the rotary knob 120 of the control wheel 106 also may include a light ring 188 positioned within the outer housing provided by the rotary knob 120 and circumferential to the button 122. The light ring 188 can be programmed or operated to be illuminated in a sequence of illumination to inform of a status of the injection. In other examples, the light ring 188 is programmed or operated to change color to reflect pressure on the button 122, and pressure applied to the button 122 is received and used to adjust a speed of injection during injection (e.g., a higher pressure results in a higher speed of injection). A color of the light ring 188 also changes at an end of the injection to inform the user of completion of the injection.

Examples of possible illumination of the light ring 188 includes a first illumination to indicate an end of injection, a second illumination to indicate a cartridge end, a third illumination to indicate speed control, a fourth illumination to indicate a low battery, a fifth illumination to indicate a full battery, a sixth illumination to indicate charging the battery, etc. Each illumination can be differentiated via intensity of light and/or via a color change due to usage of a light emitting diode (LED) or other light source, for example.

Figure 21:
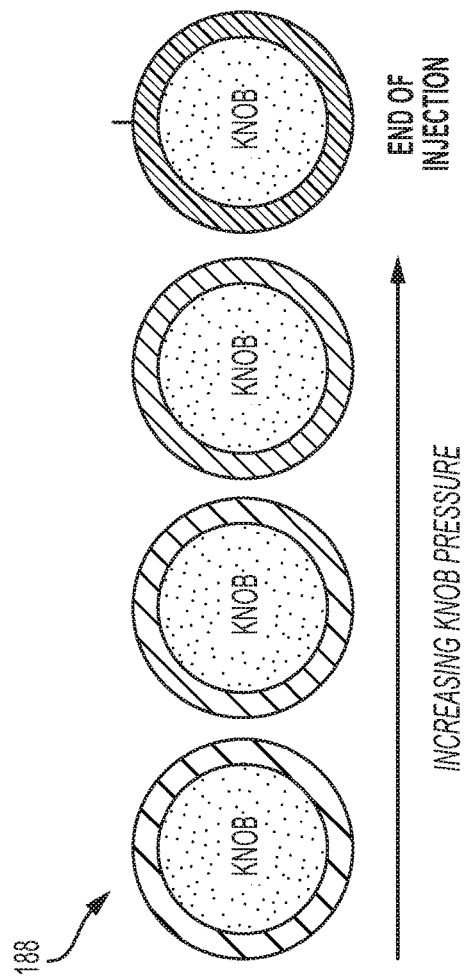
FIG. 21 is an example illustration of a sequence of illumination of the light ring, according to an example implementation.

FIG. 21 is an example illustration of a sequence of illumination of the light ring 188, according to an example implementation. Illumination of the light ring 188 provides indications of a dose set and an amount of medicament being injected during the injection. An example functionality includes without any dose set, the light ring 188 is illuminated a first color (e.g., green), and once a dose is set, the light ring 188 is illuminated a second color (blue).

Rotation of the outer housing of the rotary knob 120 causes the light ring 188 to be illuminated a first color and at an intensity level based on an amount of rotation of the outer housing of the rotary knob 120. An amount of rotation of the outer housing of the rotary knob 120 is related to an amount of medicament being injected during the injection. Once the injection is completed, the light ring 188 is illuminated a second color.

An example illumination sequence is shown in FIG. 21. Once the user starts to press on the rotary knob 120, the motor 124 starts to work. The light ring 188 lights up blue and becomes darker with a higher force of pressure applied to the button 122 and the motor 124 works faster. Once the set dose is expelled (end of injection), the motor 124 stops and the circular light turns into green to indicate end.

The light ring 188 may include a string of LEDs all connected in one circuit. In other examples, the light ring 188 may include one light source and a reflective surface over the light source that causes display to be visualized in a sequence. Still further, the light ring 188 may include one or more light sources positioned to be circumferential to the rotary knob 122 that are illuminated in a sequence of illumination to inform of a status of the injection. With use of multiple light sources, the light sources may be mounted at an angle of 60° to each other, for example.

Figure 22:
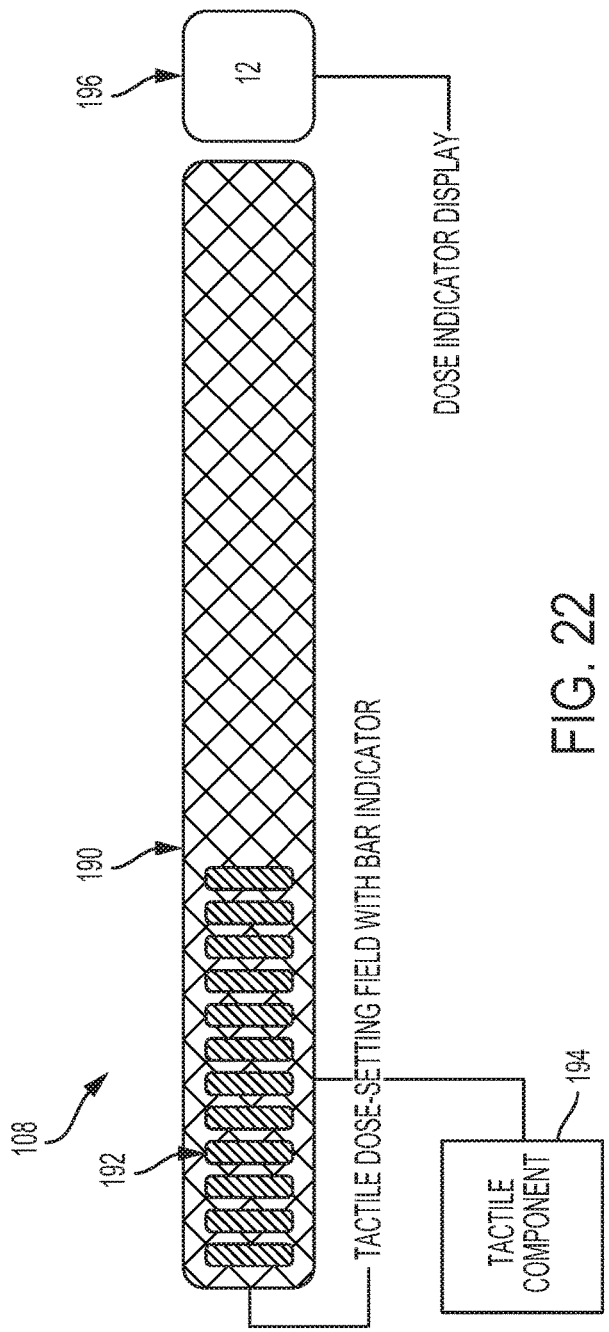
FIG. 22 is an illustration of another example of the display, according to an example implementation.

FIG. 22 is an illustration of another example of the display 108, according to an example implementation. In this example, the display 108 includes a tactile dose setting functionality and bar indicator for display of dose. For example, the display 108 include a tactile dose-setting field 190 for receiving a sliding contact input to set a dosing quantity for an injection, and the tactile dose-setting field 190 includes a display area for indicating the dosing quantity with graphical indicators 192. The injector 100 also includes a tactile component 194 coupled to the tactile dose-setting field 190 for providing force, motion, or vibration feedback based on receipt of the sliding contact at the tactile dose-setting field 190.

The display 108 further includes a dose indicator display 196 coupled or proximal to the tactile dose-setting field 190 for displaying the dosing quantity based on the sliding contact input.

The tactile dose-setting field 190 is configured to receive the sliding contact input in a linear motion along a first direction and a second direction, where the second direction is opposite the first direction. For example, receipt of the sliding contact input in the first direction increases the dosing quantity and receipt of the sliding contact input in the second direction decreases the dosing quantity. Every dose set is visually marked by a red bar or other type of graphical indicators 192, and tactile feedback is provided to the user via the tactile component 194. The dose indicator display 196 also shows a total number of units selected, for example.

The tactile component 194 may include a vibrating component to vibrate the injector 100 so as to provide feedback to the user.

Within examples, the injector 100 may include the tactile dose-setting field 190 in addition to the rotary knob 120. In other examples, the injector 100 may include one of the tactile dose-setting field 190 or the rotary knob 120.

FIG. 23 is an illustration of example digital display characters, according to an example implementation. The display 108 and/or the dose indicator display 196 may include a four digits display, and symbols can be illustrated and defined as shown in FIG. 23 to indicating priming, replace cartridge, the recent injected dose, the time since last injection, remaining units in the medicament, units set, error, and battery low, for example.

Figure 24:
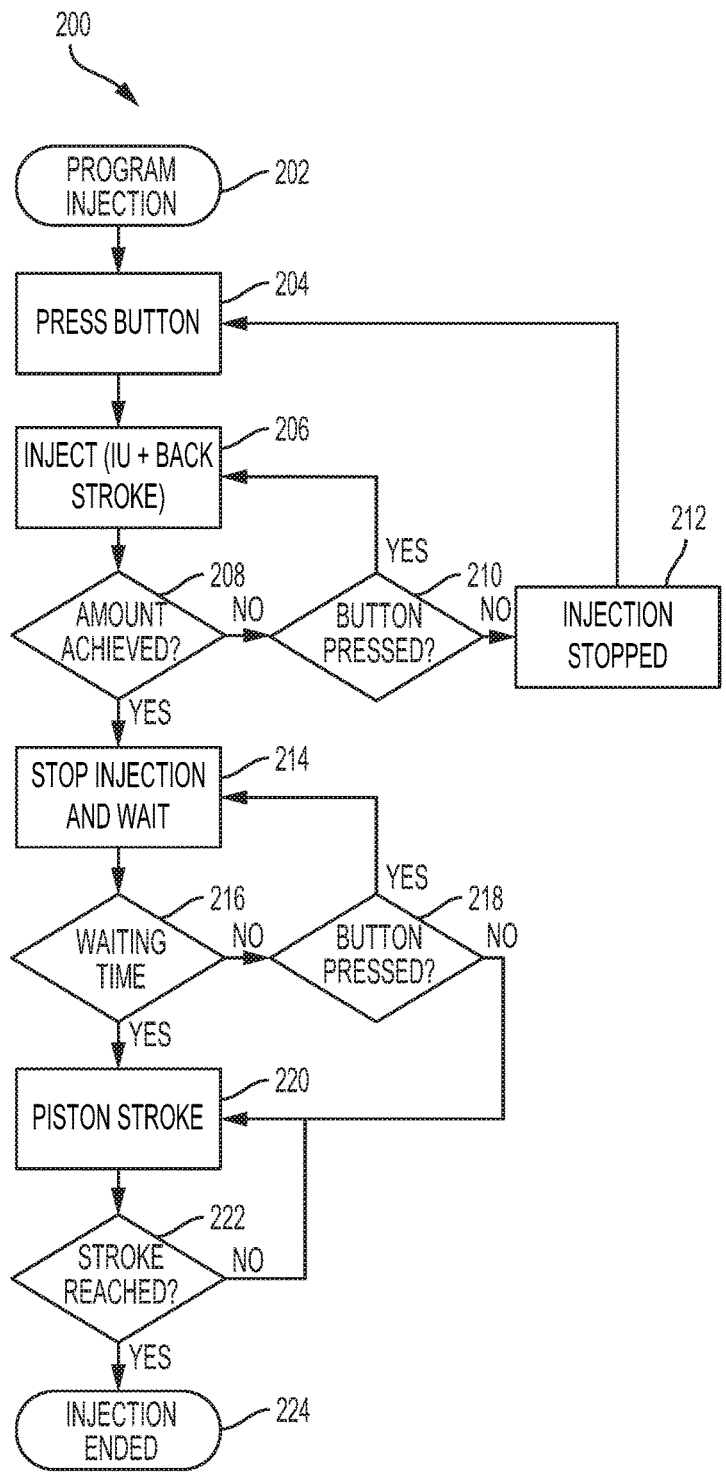
FIG. 24 shows a flowchart of an example method for an injection procedure using the injector, according to an example implementation.

FIG. 24 shows a flowchart of an example method 200 for an injection procedure using the injector 100, according to an example implementation. Method 200 shown in FIG. 24 presents an example of a method that could be used with the injector 100, for example. Further, the injector 100 or components of the injector 100 may be used or configured to perform logical functions presented in FIG. 24. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 200 may include one or more operations, functions, or actions as illustrated by one or more of blocks 202-224. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, some blocks may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, some blocks in FIG. 24, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 202, the method 200 includes programming the injection using the rotary knob 120 of the injector 100. At block 204, the user presses the button 122 to start the injection. At block 206, injection occurs, and at block 208, the processor 128 determines if the set quantity amount has been achieved via outputs from the encoder 126 that is monitoring the motor 124, for example. If not, at block 210, the processor 128 determines if the button 122 has been pressed to pause the injection. If the button 122 has not been pressed, at block 212, the injection is determined to have been stopped or interrupted (possibly due to running out of medicament), in which case the medicament is replaced and the button 122 is pressed again (at block 204) to restart the injection. If the button 122 was pressed, injection continues at block 206.

If the amount is achieved, as shown at block 208, then the injection stops as shown at block 214, for a waiting time. During the waiting time, as shown at block 216, it is determined if the button 122 is pressed at block 218, and if so, the injection remains stopped. If not, and the waiting time expires, the piston strokes back, as shown at block 220. Once the piston stroke is reached, at block 222, the injection is ended at block 224.

Using the method 200 enables a high dose accuracy to be achieved. In some examples, an end stop position can be set (e.g., end of cartridge), and a start position can be set (e.g., plunger position in new cartridge) for further preferences. Furthermore, one the button 122 is pressed, an amount of the dosage can be set to be fixed or have maximum amounts that can be administered for safety.

FIG. 24 also shows an example of contents of the display 108 during the method 200.

Figure 25:
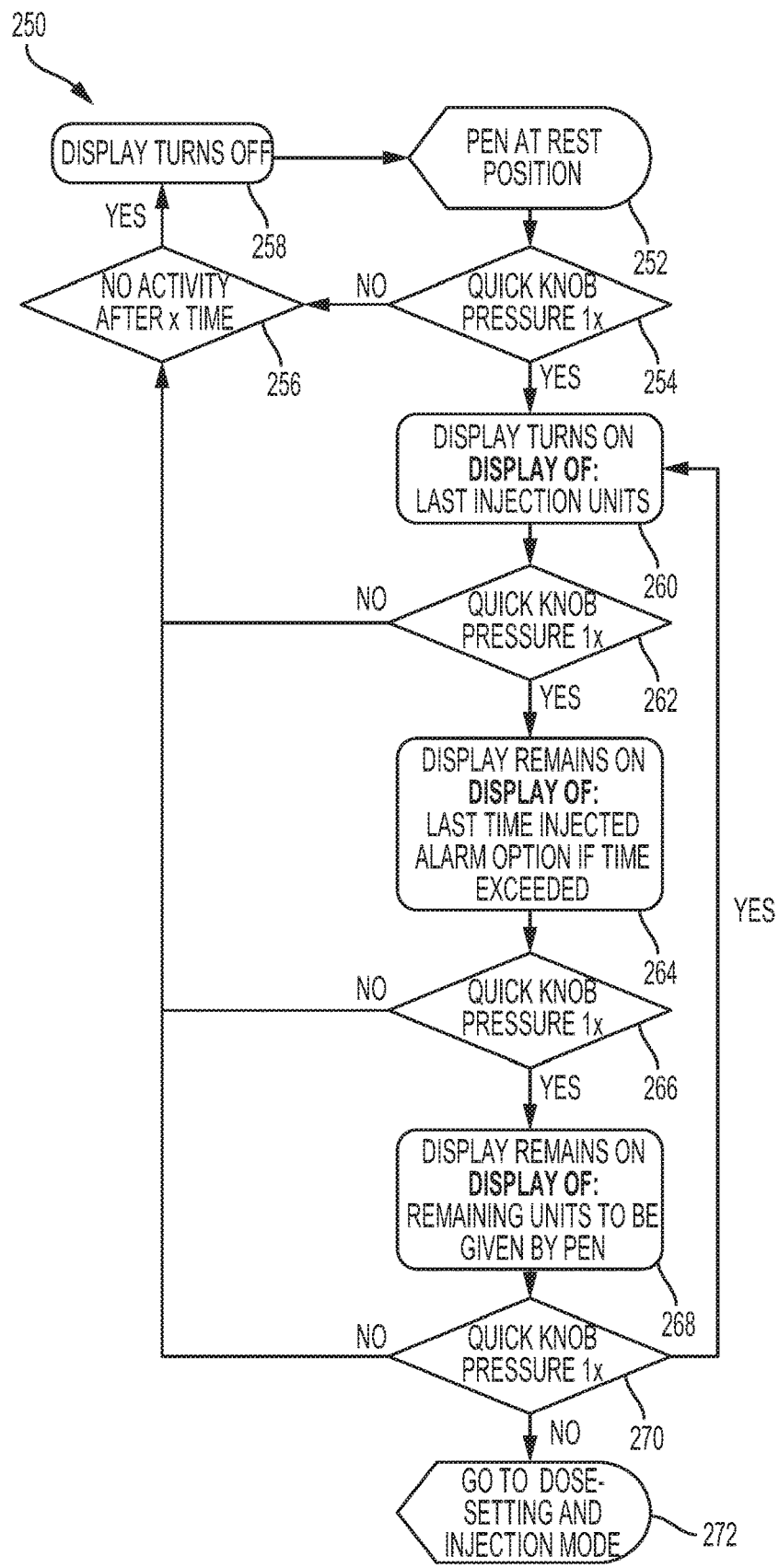
FIG. 25 shows a flowchart of an example method for use of the injector in an information mode, according to an example implementation.

FIG. 25 shows a flowchart of an example method 250 for use of the injector 100 in an information mode, according to an example implementation. As mentioned above, it should be understood that for this and other processes and methods disclosed herein, flowcharts show functionality and operation of one possible implementation of present examples. In this regard, some blocks may represent a module, a segment, or a portion of program code, which includes one or more instructions executable by a processor for implementing specific logical functions or steps in the process.

At block 252, the injector 100 is at a rest position, and at block 254, a quick knob pressure is detected via rotation of the rotary knob 120. However, if no knob rotation is detected, and no activity after a threshold time limit as shown at block 256, the display 108 turns off, as shown at block 258.

Based on detection of rotation of the rotary knob 120, the display 108 turns on and displays information about a last injection, as shown at block 260. Following, based on additional knob rotation, as shown at block 262, the display remains on and updates display of content to a last time injected to inform the user of such information, as shown at block 264. Based on another additional knob rotation, as shown at block 266, the display remains on and displays remaining units to be given by the injector 100, as shown at block 268. Based on a yet further additional knob rotation, as shown at block 270, the processor 128 initiates the dose-setting and injection mode as shown at block 272.

It is noted that within the method 250 shown in FIG. 25, blocks 254, 256, 262, 266, and 270 are actions performed by a user to rotate the rotary knob 120, and remaining blocks illustrate functions performed by the injector 100. Thus, in the information mode, via a quick knob pressure of the rotary knob 120, a user can read the relative time and amount of the last injection, read the units remaining in the cartridge, read "live" the dose set as well as corrected dose until injection, hear an end-of-injection signal, and is informed about priming mode following a change of cartridge.

Figure 26:
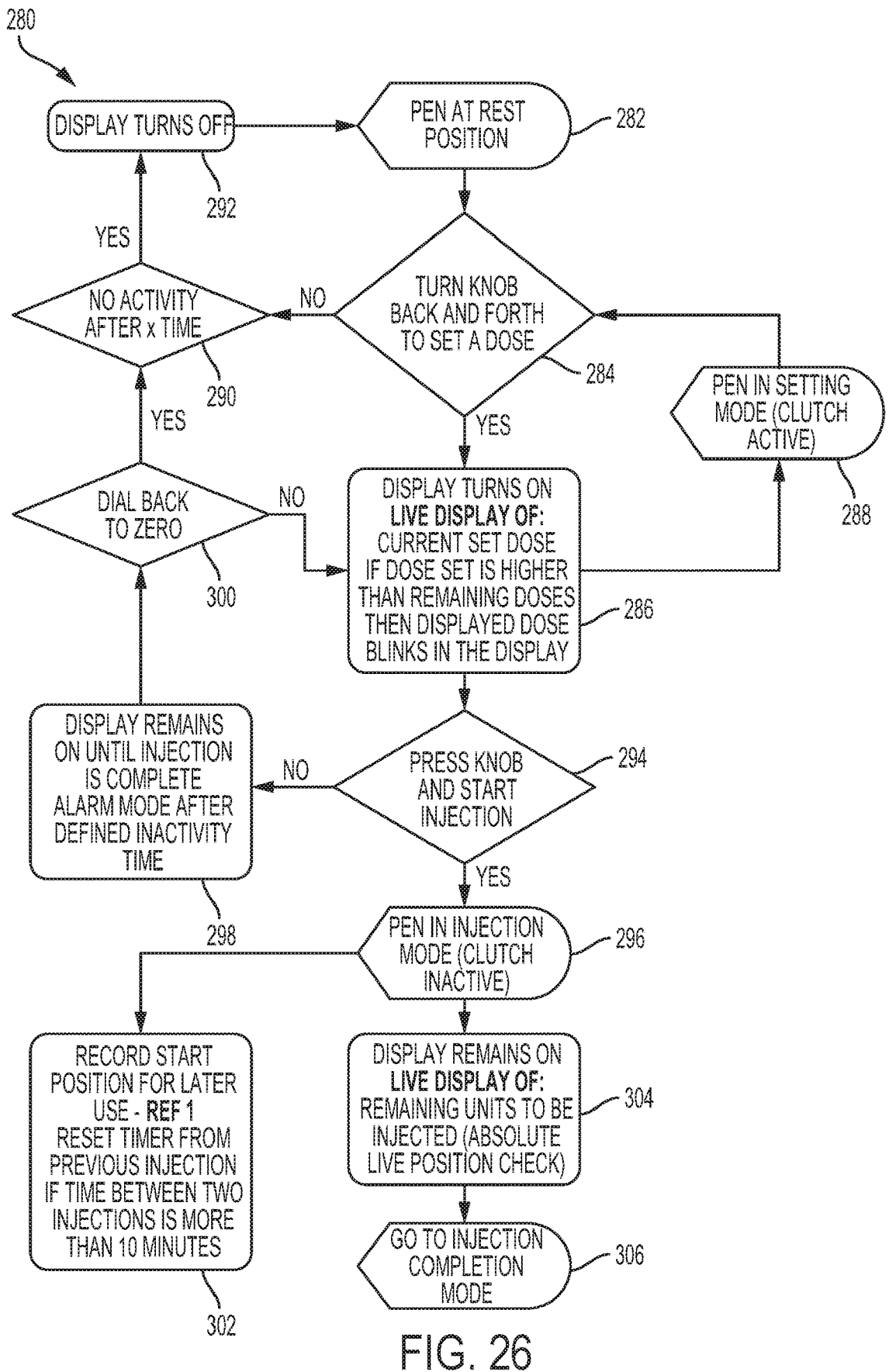
FIG. 26 shows a flowchart of an example method for use of the injector in a dose-setting and injection mode, according to an example implementation.

FIG. 26 shows a flowchart of an example method 280 for use of the injector 100 in a dose-setting and injection mode, according to an example implementation. As mentioned above, it should be understood that for this and other processes and methods disclosed herein, flowcharts show functionality and operation of one possible implementation of present examples. In this regard, some blocks may represent a module, a segment, or a portion of program code, which includes one or more instructions executable by a processor for implementing specific logical functions or steps in the process.

At block 282, the injector 100 is at a rest position. Based on detection of the rotary knob 120 being turned back and forth to set a dose as shown at block 284, the display turns on and displays a current set dose (which if the dose set is higher than remaining doses, then display dose blinks in the display 108), as shown at block 286. The injector 100 is then in setting mode (clutch active), as shown at block 288.

In absence of detection of the rotary knob 120 being turned back and forth, and following an expiration of time at which no activity is detected as shown at block 290, the display 108 turns off as shown at block 292.

Once in setting mode, based on detection of the button 122 being pressed, as shown at block 294, the injector 100 is placed into injection mode (clutch inactive), as shown at block 296. At block 294, if the button 122 is not pressed, the display 108 remains on until injection is complete and the injector 100 enters an alarm mode after defined inactivity time, as shown at block 298.

While in injection mode, the injector 100 records a start position for later use (REF 1), and resets the timer from previous injection if time between two injections is more than ten minutes, as shown at block 302. The display 108 remains on and displays contents including remaining units to be injected (absolute live position check), as shown at block 304. The injector 100 then moves to injection completion mode, as shown at block 306.

It is noted that within the method 280 shown in FIG. 26, blocks 284, 290, 294, and 300 are actions performed by a user to rotate the rotary knob 120 and/or press the button 122, and remaining blocks illustrate functions performed by the injector 100.

Figure 27:
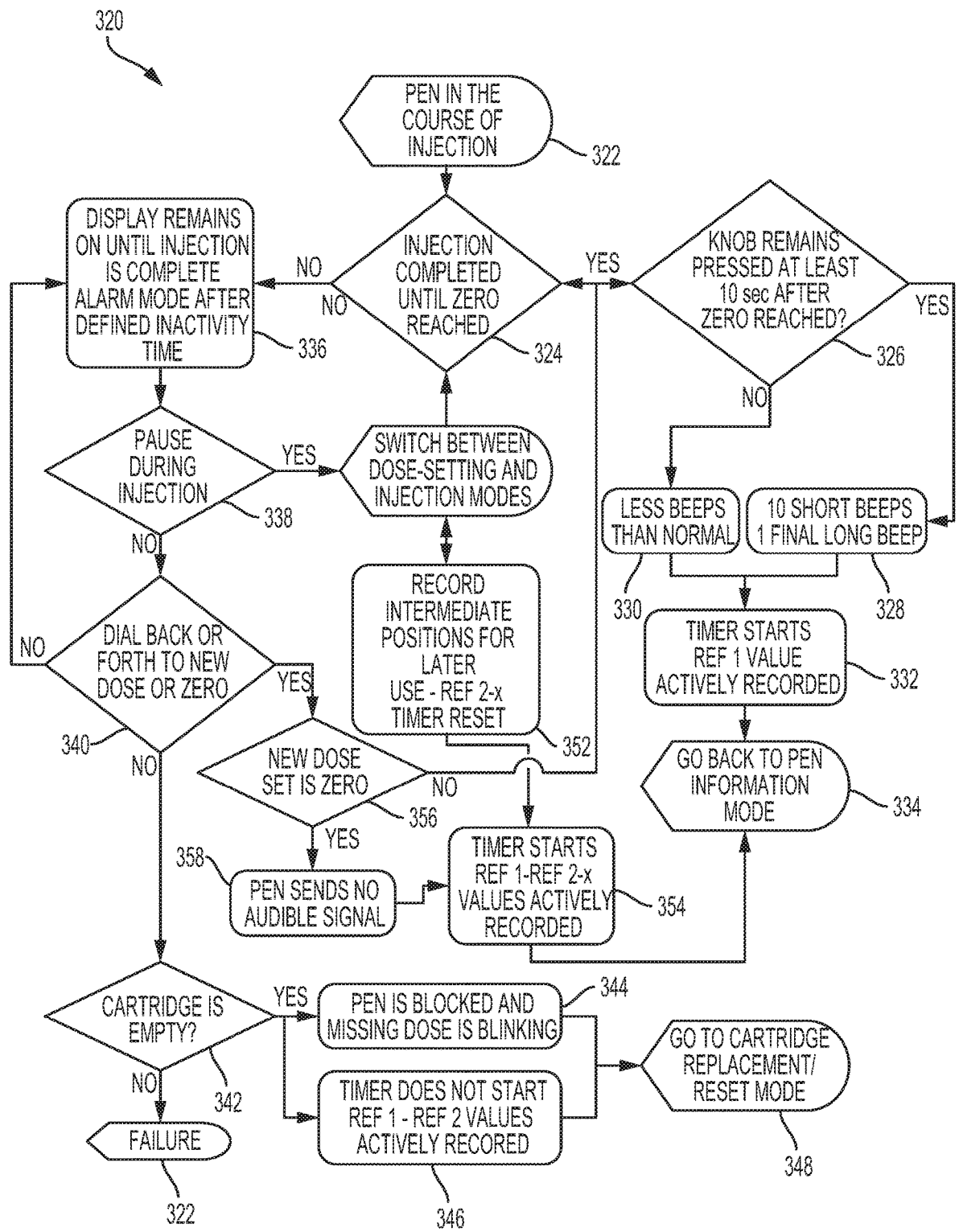
FIG. 27 shows a flowchart of an example method for use of the injector in an injection completion mode, according to an example implementation.

FIG. 27 shows a flowchart of an example method 320 for use of the injector 100 in an injection completion mode, according to an example implementation. As mentioned above, it should be understood that for this and other processes and methods disclosed herein, flowcharts show functionality and operation of one possible implementation of present examples. In this regard, some blocks may represent a module, a segment, or a portion of program code, which includes one or more instructions executable by a processor for implementing specific logical functions or steps in the process.

At block 322, the injector 100 is in the course of an injection. Once the injection is completed as shown at block 324, and the button 122 remains pressed at least ten seconds after zero is reached as shown at block 326, the injector 100 causes ten short audible beeps and one final long beep (using a speaker, for example, of the injector 100), as shown at block 328. If the button 122 does not remain pressed, at block 330, the injector 100 may causes a fewer number of beeps to inform the user that the injection is completed. At block 332, a time then starts and (REF 1) value is actively recorded to be used to determine a last injection time once a subsequent injection is started. The injector 100 then returns to information mode, as shown at block 334.

At block 324, if the injection is not yet completed, then the display 108 remains on until the injection is completed and the injector 100 enters an alarm mode after a defined inactivity time, as shown at block 336. If the injector 100 is not paused during injection as shown at block 338, and the rotary knob 120 is not dialed back or forth to a new dose or zero as shown at block 340, then the functionality returns to block 336 and the display 108 remains on until the injection is completed and the injector 100 enters an alarm mode after a defined inactivity time. Alternatively, when the cartridge is empty, as shown at block 342, the injector 100 is blocked and missing dose is blinking as shown at block 344. In addition, the timer does not start REF1-REF2 values as shown at block 346. The injector 100 then enters cartridge replacement/reset mode, as shown at block 348.

If the injector 100 is not paused during injection as shown at block 338, then the injector 100 switches between dose-setting and injection modes as shown at block 350, and records intermediate positions for later use (e.g., REF 2-x and timer reset) as well as the timer starts REF1-REF2-x to record values, as shown at blocks 352 and 354.

Returning to block 340, if the rotary knob 120 is dialed back or forth, then anew dose is set to zero, as shown at block 356, and the injector 100 sends no audible signals as shown at block 358.

It is noted that within the method 320 shown in FIG. 27, blocks 324, 326, 338, 340, 342, and 356 are actions performed by a user to rotate the rotary knob 120 and/or press the button 122, and remaining blocks illustrate functions performed by the injector 100. In FIG. 27, during injection completion mode, if the injection paused, positions are recorded, and a sequence of timer/beeps are used to inform the user of completion of the injection.

Figure 28:
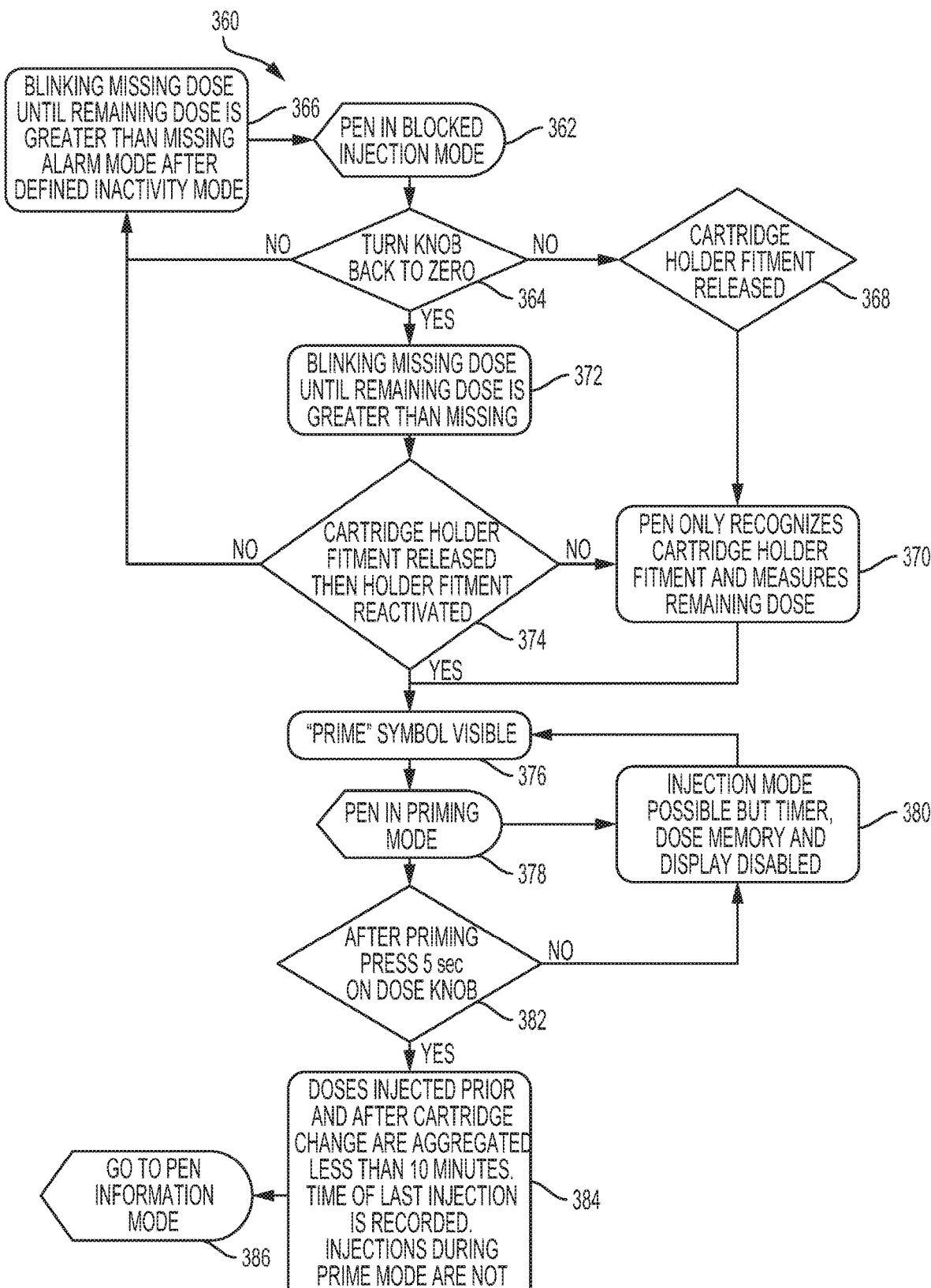
FIG. 28 shows a flowchart of an example method for use of the injector in a cartridge replacement/reset mode, according to an example implementation.

FIG. 28 shows a flowchart of an example method 360 for use of the injector 100 in a cartridge replacement/reset mode, according to an example implementation. As mentioned above, it should be understood that for this and other processes and methods disclosed herein, flowcharts show functionality and operation of one possible implementation of present examples. In this regard, some blocks may represent a module, a segment, or a portion of program code, which includes one or more instructions executable by a processor for implementing specific logical functions or steps in the process.

At block 362, the injector 100 is in block injection mode, and if the rotary knob 120 is not turned back to zero as shown at block 364, then the injector 100 blinks missing dose on the display 108 until a remaining dose is greater than missing and an alarm mode is entered after a defined inactivity mode as shown at block 366. In addition, the cartridge holder fitment is released as shown at block 368, and the injector 100 only recognizes cartridge holder fitment and measures remaining doses as shown at block 370.

If the rotary knob 120 is turned back to zero at block 364, the injector 100 blinks missing dose on the display 108 until a remaining dose is greater than missing as shown at block 372, and the cartridge holder fitment is released and the holder fitment reactivated, as shown at block 374.

The injector 100 then makes the "prime" symbol visible, as shown at block 376, and the injector 100 enter priming mode, as shown at block 378. As shown at block 380, the injection mode is possible at this stage, but time, dose memory, and the display 108 are disabled.

At block 382, after priming and detection of a button press of five seconds, doses injected prior and after cartridge change are aggregated if interval less than ten minutes, a time of last injection is recorded, and injections during prime mode are not recorded as shown at block 384. The injector 100 then transitions to information mode, as shown at block 386.

It is noted that within the method 360 shown in FIG. 28, blocks 364, 368, 374, and 382 are actions performed by a user to rotate the rotary knob 120 and/or press the button 122, and remaining blocks illustrate functions performed by the injector 100.

A summary of some of the program functions of the injector 100 is shown in Table 1 below.

TABLE 1

| No. | Programming Function | Comment |
|---|---|---|
| 1 | Injection | the injection is started by pressing the control button |
| 2 | Prime | the priming is started by pressing the control button |
| 3 | First Shot | the first shot is started by pressing the control button |
| 4 | Referencing | press home button to start go home |
| 5 | Sleep | by pushing the control knob for 1.5 s, the pen goes into sleep mode |
| 6 | change parameter 1 | 1. press the control knob for 1.5 s → program selection<br>2. rotate the control wheel to adjust the dosing quantity<br>3. press the control knob for 1.5 s → set value |

Figure 29:
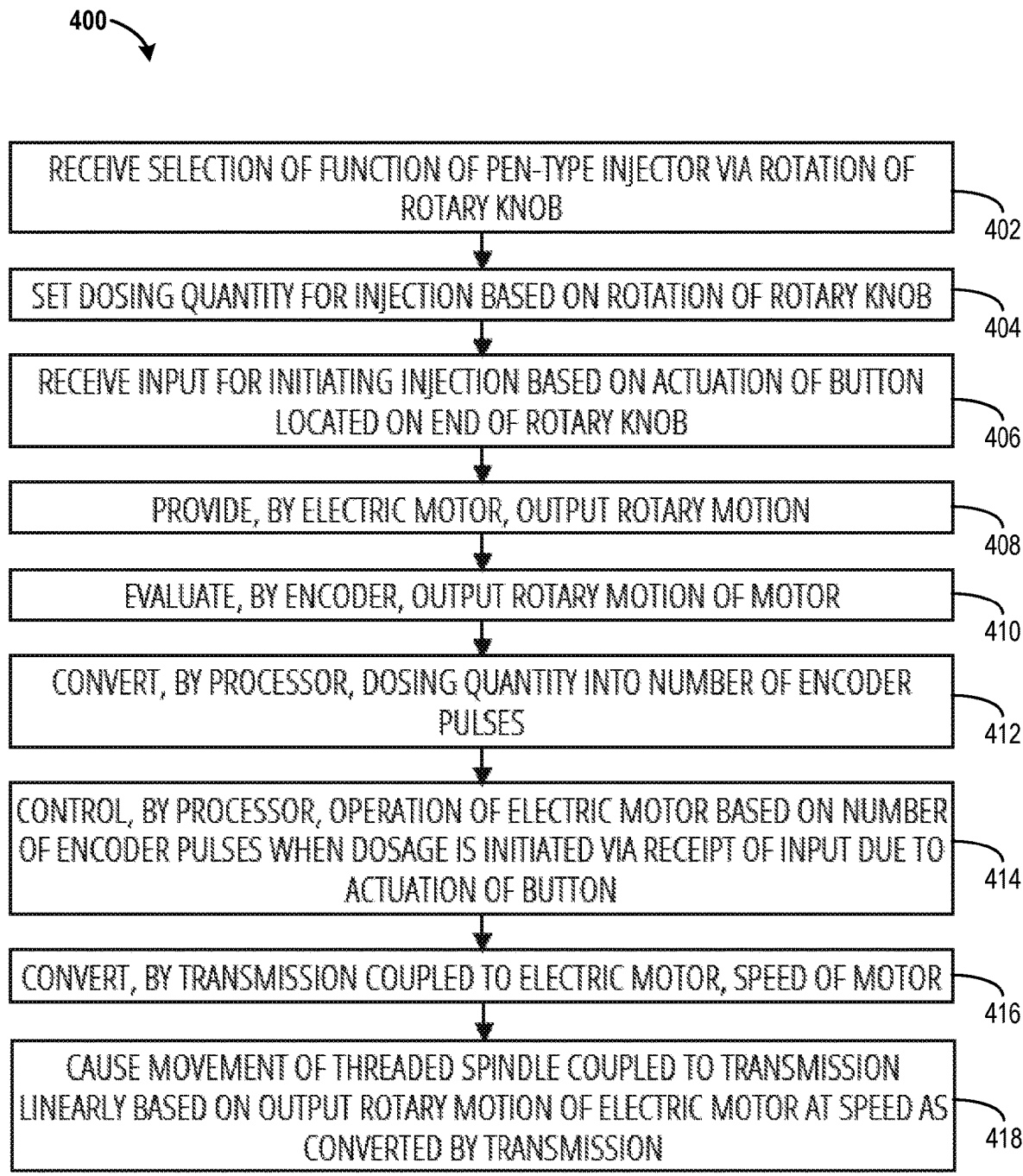
FIG. 29 shows a flowchart of an example method for operating the injector, according to an example implementation.

FIG. 29 shows a flowchart of an example method 400 for operating the injector 100, according to an example implementation. At block 402, the method 400 includes receiving a selection of a function of the injector 100 via rotation of the rotary knob 120. At block 404, the method 400 includes setting a dosing quantity for an injection based on the rotation of the rotary knob 120. At block 406, the method 400 includes receiving an input for initiating the injection based on actuation of the button 122 located on an end of the rotary knob 120. At block 408, the method 400 includes providing, by an electric motor 124, an output rotary motion. At block 410, the method 400 includes evaluating, by an encoder 126, the output rotary motion of the electric motor 124. At block 412, the method 400 includes converting, by the processor 128, the dosing quantity into a number of encoder pulses. At block 414, the method 400 includes controlling, by the processor 128, operation of the electric motor 124 based on the number of encoder pulses when dosage is initiated via receipt of the input due to actuation of the button 122. At block 416, the method 400 includes converting, by the transmission 130 coupled to the electric motor 124, a speed of the motor 124. At block 418, the method 400 includes causing movement of a threaded spindle 132 coupled to the transmission 130 linearly based on the output rotary motion of the electric motor 124 at the speed as converted by the transmission 130.

Figure 30:
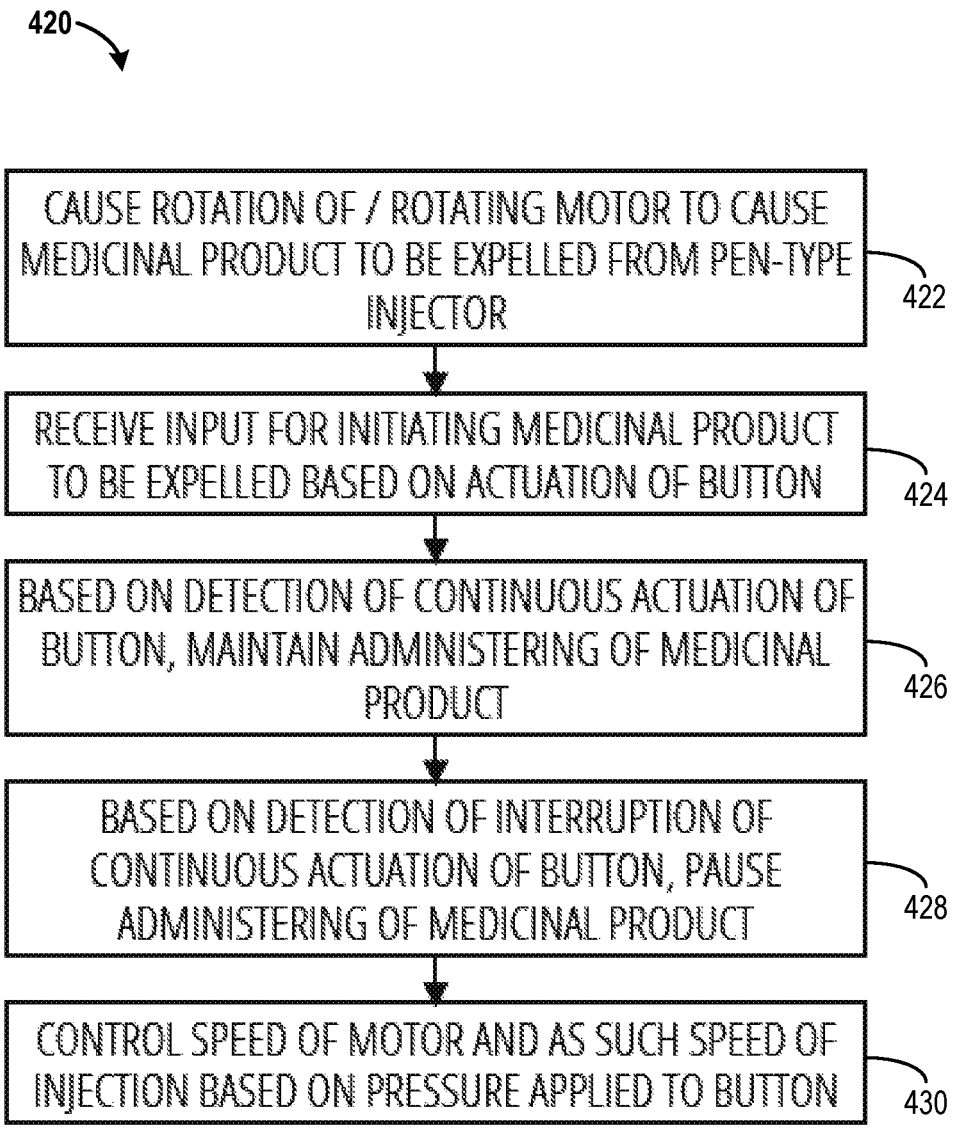
FIG. 30 shows a flowchart of another example method for operating the injector, according to an example implementation.

FIG. 30 shows a flowchart of another example method 420 for operating the injector 100, according to an example implementation. At block 422, the method 420 includes causing rotation of/rotating the motor 124 to cause a medicinal product to be expelled from the injector 100. At block 424, the method 420 includes receiving an input for initiating the medicinal product to be expelled based on actuation of the button 122. At block 426, the method 420 includes based on detection of a continuous actuation of the button 122, maintaining administering of the medicinal product. At block 428, the method 420 includes based on detection of an interruption of the continuous actuation of the button 122, pausing administering of the medicinal product. At block 430, the method 420 includes controlling a speed of the motor 124 and as such a speed of injection based on a pressure applied to the button 122.

Figure 31:
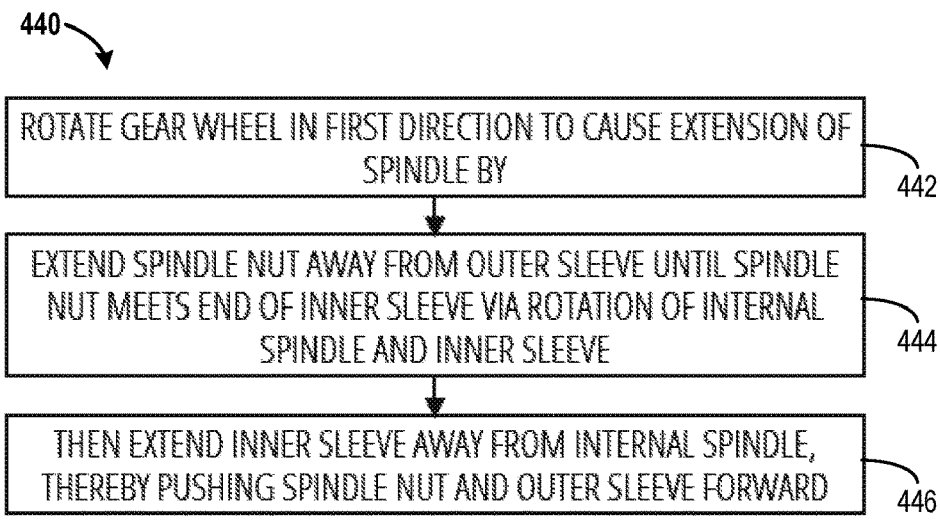
FIG. 31 shows a flowchart of an example method for operating a spindle for an injector, according to an example implementation.

FIG. 31 shows a flowchart of an example method 440 for operating a spindle for a injector 100, according to an example implementation. The spindle 132 includes the gear wheel 160, an internal spindle 162 coupled to the gear wheel 160 that is threaded along a length of the internal spindle 162, an inner sleeve 172 including internal threads for mating with threads of the internal spindle for positioning the internal spindle into the inner sleeve, a spindle nut 164 including internal threads for mating with external threads of the inner sleeve for positioning the inner sleeve into the spindle nut, and an outer sleeve 174 into which the spindle nut, the inner sleeve, and the internal spindle are positioned in a retracted state. At block 442, the method 440 includes rotating the gear wheel in a first direction to cause extension of the spindle by extending the spindle nut away from the outer sleeve until the spindle nut meets an end of the inner sleeve via rotation of the internal spindle and the inner sleeve as shown at block 444, and then extending the inner sleeve away from the internal spindle, thereby pushing the spindle nut and the outer sleeve forward as shown at block 446.

Figure 32:
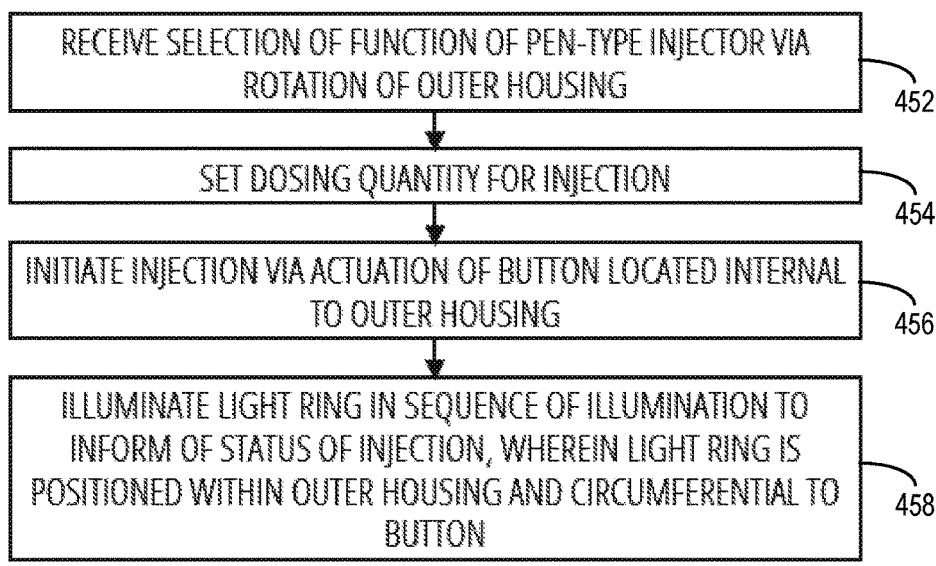
FIG. 32 shows a flowchart of an example method for operating a rotary knob for an injector, according to an example implementation.

FIG. 32 shows a flowchart of an example method 450 for operating a rotary knob for a pen-type injector. At block 452, the method 450 includes receiving a selection of a function of the injector 100 via rotation of an outer housing. At block 454, the method 450 includes setting a dosing quantity for an injection. At block 456, the method 450 includes initiating the injection via actuation of the button 122 located internal to the outer housing. At block 458, the method 450 includes illuminating the light ring 188 in a sequence of illumination to inform of a status of the injection, wherein the light ring 188 is positioned within the outer housing and circumferential to the button 122.

Figure 33:
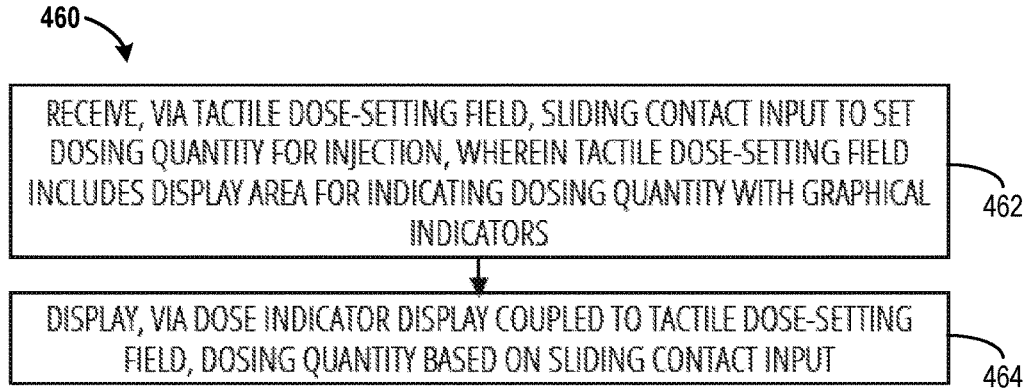
FIG. 33 shows a flowchart of an example method for operating the injector, according to an example implementation.

FIG. 33 shows a flowchart of an example method 460 for operating the injector 100. At block 462, the method 460 includes receiving, via the tactile dose-setting field 190, a sliding contact input to set a dosing quantity for an injection, wherein the tactile dose-setting field includes the display area for indicating the dosing quantity with graphical indicators 192. At block 464, the method 460 includes displaying, via a dose indicator display 108 coupled to the tactile dose-setting field, the dosing quantity based on the sliding contact input.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

Embodiments of the present disclosure can thus relate to one of the enumerated example embodiment (EEEs) listed below.

EEE 1 is an injector comprising: a rotary knob for selecting a function of the injector and setting a dosing quantity for an injection; a button located on an end of the rotary knob for initiating the injection; an electric motor providing an output rotary motion; an encoder for evaluating the output rotary motion of the motor; a processor coupled to the rotary knob, the button, the electric motor, and the encoder, wherein the processor receives the selected function of the injector and the dosing quantity for the injection from the rotary knob and receives a signal from the button for initiating the injection and converts the dosing quantity into a number of encoder pulses, wherein the processor controls operation of the motor based on the number of encoder pulses when dosage is triggered via receipt of the signal from the button for initiating the injection; a transmission coupled to the electric motor to convert a speed of the motor; and a threaded spindle coupled to the transmission, wherein the threaded spindle moves linearly based on the output rotary motion of the motor at the speed as converted by the transmission.

EEE 2 is the injector of EEE 1, further comprising a punch connected to an end of the threaded spindle, wherein linear movement of the spindle causes the punch to release medicament.

EEE 3 is the injector of any of EEEs 1-2, wherein the transmission comprises a multi-stage spur gear.

EEE 4 is the injector of any of EEEs 1-3, wherein the encoder comprises: an encoder disk with segmented windows that is positioned on a shaft of the motor; and a fork light barrier.

EEE 5 is the injector of any of EEEs 1-4, wherein the rotary knob is rotatable to select functions including a mode of the injector and a menu.

EEE 6 is the injector of any of EEEs 1-5, wherein the rotary knob is lockable to lock against unintentional switching on.

EEE 7 is the injector of any of EEEs 1-6, wherein the button is configured to be actuated for saving one or more values selected via the rotary knob.

EEE 8 is the injector of any of EEEs 1-7, wherein the button is configured to be actuated for powering the injector on and off.

EEE 9 is the injector of any of EEEs 1-8, further comprising: a housing, wherein the electric motor, the encoder, the processor, the transmission, and the threaded spindle are included within the housing.

EEE 10 is the injector of EEE 8, further comprising a digital display coupled to the housing, wherein the housing includes a back and two side portions, and wherein the digital display is coupled to the two side portions to enclose the housing.

EEE 11 is the injector of any of EEEs 1-10, further comprising: a display merged with an outer body of the injector.

EEE 12 is the injector of any of EEEs 1-11, further comprising: a memory, wherein the memory stores instructions that when executed by the processor, causes the processor to control operation of the motor.

EEE 13 is the injector of EEE 11, wherein the memory stores values including an injection history, a punch position, and user values.

EEE 14 is the injector of any of EEEs 1-13, further comprising a real-time clock (RTC) module coupled to the processor.

EEE 15 is the injector of any of EEEs 1-14, further comprising a battery.

EEE 16 is the injector of EEE 14, further comprising: a universal serial bus (USB) interface coupled to the battery and the processor.

EEE 17 is a injector comprising a motor, whereby rotation of the motor causes a medicinal product to be expelled; a button, which is pressed to initiate and maintain the injection, whereby pressure applied to the button during injection changes a speed of the motor and as such a speed of injection.

EEE 18 is a spindle for an injector, comprising: a gear wheel; an internal spindle coupled to the gear wheel, wherein the internal spindle is threaded along a length of the internal spindle; an inner sleeve, wherein the inner sleeve includes internal threads for mating with threads of the internal spindle for positioning the internal spindle into the inner sleeve, and wherein the inner sleeve includes external threads; a spindle nut, wherein the spindle nut includes internal threads for mating with the external threads of the inner sleeve for positioning the inner sleeve into the spindle nut; and an outer sleeve into which the spindle nut, the inner sleeve, and the internal spindle are positioned in a retracted state, wherein the outer sleeve includes an anti-rotation component, wherein rotation of the gear wheel in a first direction causes extension of the spindle by: extending the spindle nut away from the outer sleeve until the spindle nut meets an end of the inner sleeve via rotation of the internal spindle and the inner sleeve; and then extending the inner sleeve away from the internal spindle, thereby pushing the spindle nut and the outer sleeve forward.

EEE 19 is the spindle of EEE 18, wherein the internal spindle includes a locking plate at an end of the internal spindle, wherein the locking plate prevents the internal spindle from being unscrewed from the inner sleeve.

EEE 20 is the spindle of any of EEEs 18-19, where the inner sleeve is freely rotatable.

EEE 21 is the spindle of any of EEEs 18-20, wherein rotation of the gear wheel in a second direction that is reverse of the first direction causes retraction of the spindle in an inverse order of the extension.

EEE 22 is a rotary knob for an injector, comprising: an outer housing rotatable for selecting a function of the injector and setting a dosing quantity for an injection; a button located internal to the outer housing that is actuatable for initiating the injection; and a light ring positioned within the outer housing and circumferential to the button, wherein the light ring is illuminated in a sequence of illumination to inform of a status of the injection.

EEE 23 is the rotary knob of EEE 22, wherein illumination of the light ring provides indications of a dose set and an amount of medicament being injected during the injection.

EEE 24 is the rotary knob of any of EEEs 22-23, wherein without any dose set, the light ring is illuminated a first color, and once a dose is set, the light ring is illuminated a second color.

EEE 25 is the rotary knob of any of EEEs 22-24, wherein rotation of the outer housing causes the light ring to be illuminated a first color and at an intensity level based on an amount of rotation of the outer housing, wherein an amount of rotation of the outer housing is related to an amount of medicament being injected during the injection, and once the injection is completed, the light ring is illuminated a second color.

EEE 26 is the rotary knob of any of EEEs 22-25, wherein, rotation of the outer housing causes the light ring to be illuminated a first color and at an intensity level based on an amount of rotation of the outer housing.

EEE 27 is the rotary knob of any of EEEs 22-26, wherein a pressure on the button during injection causes the light ring to be illuminated at an intensity level based on the pressure on the button.

EEE 28 is a pen-type injector, comprising: a tactile dose-setting field for receiving a sliding contact input to set a dosing quantity for an injection, wherein the tactile dose-setting field includes a display area for indicating the dosing quantity with graphical indicators; and a dose indicator display coupled to the tactile dose-setting field for displaying the dosing quantity based on the sliding contact input.

EEE 29 is the pen-type injector of EEE 28, further comprising a tactile component coupled to the tactile dose-setting field for providing force, motion, or vibration feedback based on receipt of the sliding contact at the tactile dose-setting field.

EEE 30 is the pen-type injector of any of EEEs 28-29, wherein the tactile dose-setting field is configured to receive the sliding contact input in a linear motion along a first direction and a second direction, wherein the second direction is opposite the first direction.

EEE 31 is the pen-type injector of any of EEEs 28-30, wherein receipt of the sliding contact input in the first direction increases the dosing quantity and receipt of the sliding contact input in the second direction decreases the dosing quantity.

EEE 32 is an injector comprising: a rotary knob having an outer housing rotatable for selecting a function of the injector and setting a dosing quantity for an injection; a button located on an end of the rotary knob and internal to the outer housing for initiating the injection; a light ring positioned within the outer housing and circumferential to the button, wherein the light ring is illuminated in a sequence of illumination to inform of a status of the injection; an electric motor providing an output rotary motion; an encoder for evaluating the output rotary motion of the motor; a processor coupled to the rotary knob, the button, the electric motor, and the encoder, wherein the processor receives the selected function of the injector and the dosing quantity for the injection from the rotary knob and receives a signal from the button for initiating the injection and converts the dosing quantity into a number of encoder pulses, wherein the processor controls operation of the motor based on the number of encoder pulses when dosage is triggered via receipt of the signal from the button for initiating the injection; a transmission coupled to the electric motor to convert a speed of the motor; a threaded spindle coupled to the transmission, wherein the threaded spindle moves linearly based on the output rotary motion of the motor at the speed as converted by the transmission, wherein the threaded spindle includes: a gear wheel; an internal spindle coupled to the gear wheel, wherein the internal spindle is threaded along a length of the internal spindle; an inner sleeve, wherein the inner sleeve includes internal threads for mating with threads of the internal spindle for positioning the internal spindle into the inner sleeve, and wherein the inner sleeve includes external threads; a spindle nut, wherein the spindle nut includes internal threads for mating with the external threads of the inner sleeve for positioning the inner sleeve into the spindle nut; an outer sleeve into which the spindle nut, the inner sleeve, and the internal spindle are positioned in a retracted state, wherein the outer sleeve includes an anti-rotation component, wherein rotation of the gear wheel in a first direction causes extension of the spindle by: extending the spindle nut away from the outer sleeve until the spindle nut meets an end of the inner sleeve via rotation of the internal spindle and the inner sleeve; and then extending the inner sleeve away from the internal spindle, thereby pushing the spindle nut and outer sleeve forward, and a punch connected to an end of the threaded spindle, wherein linear movement of the spindle causes the punch to release a medicament.

EEE 33 is a method of operating an injector for an injection procedure as shown in FIG. 24.

EEE 34 is a method of operating an injector in an information mode as shown in FIG. 25.

EEE 35 is a method of operating an injector in a dose-setting and injection mode as shown in FIG. 26.

EEE 36 is a method of operating an injector in an injection completion mode as shown in FIG. 27.

EEE 37 is a method of operating an injector in a cartridge replacement/reset mode as shown in FIG. 28.

What is claimed is:
1. A rotary knob for an injector, comprising:
an outer housing rotatable for selecting a function of the injector and setting a dosing quantity for an injection;
a button located internal to the outer housing that is actuatable for initiating the injection; and
a light ring positioned within the outer housing of the rotary knob and circumferential to the button,
wherein the light ring is illuminated in a sequence of illumination to inform of a status of the injection, and wherein the light ring is arranged in an end face of the button within the outer housing of the rotary knob such that the light ring is positioned at an end of the injector, the end face being remote from a side of the rotary knob that is connectable to a switch of the injector.

2. The rotary knob of claim 1, wherein the outer housing is rotatable to select functions including a mode of the injector and a menu.

3. The rotary knob of claim 1, wherein illumination of the light ring provides indications of a dose set and an amount of medicament being injected during the injection.

4. The rotary knob of claim 1, wherein:
without any dose set, the light ring is illuminated a first color, and
once a dose is set, the light ring is illuminated a second color.

5. The rotary knob of claim 1, wherein rotation of the outer housing causes the light ring to be illuminated a first color and at an intensity level based on an amount of rotation of the outer housing, wherein an amount of rotation of the outer housing is related to an amount of medicament being injected during the injection.

6. The rotary knob of claim 5, wherein once the injection is completed, the light ring is illuminated a second color.

7. The rotary knob of claim 1, wherein rotation of the outer housing causes the light ring to be illuminated a first color and at an intensity level based on an amount of rotation of the outer housing.

8. The rotary knob of claim 1, wherein a pressure on the button during injection causes the light ring to be illuminated at an intensity level based on the pressure on the button.

9. The rotary knob of claim 1, wherein a change in pressure applied to the button causes a change in color of illumination of the light ring.

10. The rotary knob of claim 1, wherein rotation of the outer housing in a first direction causes the dosing quantity to increase, and rotation of the outer housing in a second direction opposite the first direction causes the dosing quantity to decrease.

11. The rotary knob of claim 1, wherein actuation of the button to a first depth causes a first action to be initiated, and actuation of the button to a second depth more than the first depth causes initiation of the injection.

12. The rotary knob of claim 1, wherein the outer housing is lockable to lock against unintentional switching on.

13. The rotary knob of claim 1, wherein the button is configured to be actuated for saving one or more values selected via rotation of the outer housing.

14. The rotary knob of claim 1, wherein the button is configured to be actuated for powering the injector on and off.

15. An injector, comprising:
a rotary knob rotatable for selecting a function of the injector and setting a dosing quantity for an injection, the rotary knob including a button actuatable for initiating the injection; and
a light ring positioned within an outer housing of the rotary knob,
wherein the light ring is illuminated in a sequence of illumination to inform of a status of the injection, and
wherein the light ring is arranged in an end face of the button within the outer housing of the rotary knob such that the light ring is positioned at an end of the injector.

16. The injector of claim 15, wherein:
rotation of the outer housing causes the light ring to be illuminated a first color and at an intensity level based on an amount of rotation of the outer housing, wherein an amount of rotation of the outer housing is related to an amount of medicament being injected during the injection; and
once the injection is completed, the light ring is illuminated a second color.

17. The injector of claim 15, wherein rotation of the outer housing causes the light ring to be illuminated a first color and at an intensity level based on an amount of rotation of the outer housing.

18. A method for operating a rotary knob for an injector, comprising:
receiving a selection of a function of the injector via rotation of an outer housing of the rotary knob;
setting a dosing quantity for an injection based on an amount of rotation of the outer housing;
initiating the injection via actuation of a button located internal to the outer housing; and
illuminating a light ring in a sequence of illumination to inform of a status of the injection, wherein the light ring is positioned within the outer housing of the rotary knob and circumferential to the button, and the light ring is arranged in an end face of the button within the outer housing of the rotary knob such that the light ring is positioned at an end of the injector.

19. The method of claim 18, further comprising:
causing the light ring to be illuminated a first color and at an intensity level based on an amount of rotation of the outer housing, wherein an amount of rotation of the outer housing is related to an amount of medicament being injected during the injection; and
once the injection is completed, causing the light ring to be illuminated a second color.

20. The method of claim 18, further comprising:
causing the light ring to be illuminated at an intensity level based on an applied pressure to the button.

21. An injector, comprising:
a rotary knob rotatable for selecting a function of the injector from a menu of functions, and for setting a dosing quantity for an injection, the rotary knob including a button actuatable for initiating the injection;
a light ring positioned within an outer housing of the rotary knob; and
a processor coupled to the rotary knob, wherein the processor provides the menu of functions and controls operation of the injector based on the selected function of the injector and the dosing quantity for the injection received from the rotary knob,
wherein the light ring is arranged in an end face of the button within the outer housing of the rotary knob such that the light ring is positioned at an end of the injector.

22. The injector of claim 21, wherein:
the outer housing is rotatable, and
the button is located internal to the outer housing.

23. The injector of claim 21, wherein:
the light ring is positioned to be circumferential to the rotary knob and is illuminated in a sequence of illumination to inform of a status of the injection.

24. The injector of claim 21, wherein the rotary knob is actuatable for initiating the injection by being pressed into a body of the injector.

25. The injector of claim 21, further comprising:
one or more light sources positioned to be circumferential to the rotary knob, wherein the one or more light sources are illuminated in a sequence of illumination to inform of a status of the injection.

26. The rotary knob of claim 1, wherein the rotary knob is connected to the switch of the injector.

27. The rotary knob of claim 1, wherein the switch is a micro-switch that is configured to allow push button control of the button.

28. The rotary knob of claim 1, wherein the light ring is configured to change color and adjust a speed of injection based on a pressure applied to the button.

29. The rotary knob of claim 1, wherein the light ring is configured to change color at an end of the injection to inform a user of completion of the injection.

30. The rotary knob of claim 1, wherein the light ring is configured to include a plurality of illuminations including a first illumination that indicates an end of the injection, a second illumination to indicate a cartridge end, a third illumination to indicate speed control, a fourth illumination to indicate a low battery, a fifth illumination to indicate a full battery, and a sixth illumination to indicate charging of the battery.

31. The rotary knob of claim 30, wherein each of the plurality of illuminations has at least one of a different intensity of light and a different color of light.

* * * * *